(12) United States Patent
Rands et al.

(10) Patent No.: US 11,697,638 B2
(45) Date of Patent: Jul. 11, 2023

(54) 5-METHOXY-N,N-DIMETHYLTRYPTAMINE CRYSTALLINE FORMS

(71) Applicant: Small Pharma Ltd, London (GB)

(72) Inventors: Peter Rands, London (GB); Marie Claire Layzell, London (GB)

(73) Assignee: Small Pharma Ltd, London (GB)

( * ) Notice: Subject to any disclaimer, the term of this patent is extended or adjusted under 35 U.S.C. 154(b) by 7 days.

(21) Appl. No.: 17/469,063

(22) Filed: Sep. 8, 2021

(65) Prior Publication Data
US 2023/0086574 A1    Mar. 23, 2023

(51) Int. Cl.
*C07D 209/16*    (2006.01)
(52) U.S. Cl.
CPC ........ *C07D 209/16* (2013.01); *C07B 2200/05* (2013.01); *C07B 2200/13* (2013.01)
(58) Field of Classification Search
CPC .............. C07D 209/16; C07B 2200/05; C07B 2200/13
See application file for complete search history.

(56) References Cited

U.S. PATENT DOCUMENTS

| | | | |
|---|---|---|---|
| 4,336,378 A | 6/1982 | Brand et al. | |
| 8,268,856 B2 | 9/2012 | Hamann et al. | |
| 11,000,534 B1 | 5/2021 | Sippy | |
| 11,242,318 B2 | 2/2022 | Nivorozhkin et al. | |
| 2002/0022667 A1 | 2/2002 | Pace et al. | |
| 2009/0076121 A1 | 3/2009 | Czarnik | |
| 2018/0221396 A1 | 8/2018 | Chadeayne | |
| 2020/0339519 A1 | 10/2020 | Kim et al. | |
| 2020/0390746 A1 | 12/2020 | Rands et al. | |
| 2021/0378969 A1 | 12/2021 | Rands et al. | |
| 2021/0395201 A1 | 12/2021 | Rands et al. | |
| 2021/0403426 A1 | 12/2021 | Rands et al. | |
| 2022/0062237 A1 | 3/2022 | Layzell et al. | |
| 2022/0062238 A1 | 3/2022 | Layzell et al. | |
| 2022/0081396 A1 | 3/2022 | Rands et al. | |

FOREIGN PATENT DOCUMENTS

| | | | |
|---|---|---|---|
| GB | 2585978 A | 1/2021 | |
| GB | 2586940 A | 3/2021 | |
| GB | 2596884 A | 1/2022 | |
| WO | 9300333 A1 | 1/1993 | |
| WO | 02083144 A1 | 10/2002 | |
| WO | 2004085392 A1 | 10/2004 | |
| WO | 2008049116 A2 | 4/2008 | |
| WO | 2008071455 A1 | 6/2008 | |
| WO | 2008151584 A1 | 12/2008 | |
| WO | 2009049030 A1 | 4/2009 | |
| WO | 2018064465 A1 | 4/2018 | |
| WO | 2018195455 A1 | 10/2018 | |
| WO | 2019081764 A1 | 5/2019 | |
| WO | 2020169850 A1 | 8/2020 | |
| WO | 2020169851 A1 | 8/2020 | |
| WO | 2020-176597 A1 | 9/2020 | |
| WO | 2020-176599 A1 | 9/2020 | |
| WO | 2020245133 A1 | 12/2020 | |
| WO | 2021089872 A1 | 5/2021 | |
| WO | 2021089873 A1 | 5/2021 | |
| WO | WO-2021089873 A1 * | 5/2021 | ............. A61P 25/00 |
| WO | 2021116503 A2 | 6/2021 | |
| WO | 2021155470 A1 | 8/2021 | |
| WO | 2021234608 A1 | 11/2021 | |
| WO | 2022031566 A1 | 2/2022 | |

(Continued)

OTHER PUBLICATIONS

Robert B. Kargbo, 5-MeO-DMT: Potential Use of Psychedelic-Induced Experiences in the Treatment of Psychological Disorders, 2021, ACS Med. Chem. Lett., 12, 1646-1648. (Year: 2021).*
Alexander M. Sherwood, Synthesis and Characterization of 5-MeO-DMT Succinate for Clinical Use, 2020, ACS Omega, 5, 32067-32075. (Year: 2020).*
Ambinter Screening Library, Publication Date Mar. 26, 2020, Order No. Cat. Amb33838664.
Aurora Building Blocks 2, Publication Date Feb. 27, 2020, Order No. Cat A17.921.638.
MuseChem Product List, Publication Date Apr. 21, 2020, Order No. Cat. R055190.
Barker, et al., "Comparison of the Brain Levels of N N-Dimethyltryptamine and xxB B- Tetradeutero N, N-Dimethyltryptamine Following Intraperitoneal Injection", Biochemical Pharmacology, vol. 31, No. 15, Jan. 20, 1982, 4 pages.
Barker, Steven A., "N, N-Dimethyltryptamine (DMT), an Endogenous Hallucinogen: Past, Present, and Future Research to Determine Its Role and Function", Frontiers in Neuroscience, vol. 12, Article 536, Aug. 6, 2018, pp. 1-17.

(Continued)

*Primary Examiner* — Mark L Shibuya
*Assistant Examiner* — Luisalberto Gonzalez
(74) *Attorney, Agent, or Firm* — Heslin Rothenberg Farley & Mesiti, P.C.

(57) ABSTRACT

Described herein are crystalline fumarate salts having a Formula I, pharmaceutical formulations comprising the same, methods for their production, and uses thereof, Formula I comprising:

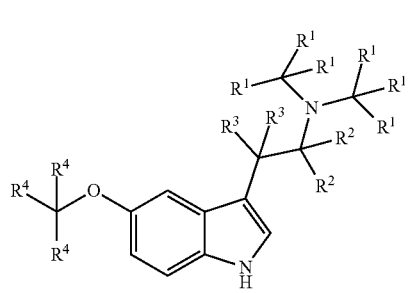

wherein each $R^1$ is independently selected from protium and deuterium; each $R^2$ is independently selected from protium and deuterium; each $R^3$ is independently selected from protium and deuterium; and each $R^4$ is independently selected from protium and deuterium; and wherein the compound has a PXRD pattern comprising characteristic peaks at 19.2±0.2 and 24.7±0.2 degrees 2-theta.

19 Claims, 10 Drawing Sheets

(56) References Cited

FOREIGN PATENT DOCUMENTS

| | | |
|---|---|---|
| WO | 2022043227 A1 | 3/2022 |
| WO | 2022069690 A2 | 4/2022 |

OTHER PUBLICATIONS

Beaton, et al., "A Comparison of the Behavioral Eeffects of Proteo- and Deurero-N, N-Dimethrltryptamine", Pharmacology, Biochemistry & Behavior, vol. 16, Sep. 8, 1982, 4 pages.

Brandt, et al., "Microwave-Accelerated Synthesis of Psychoactive Deuterated N, N-Dialkylated-[α, α, β, β-d4]-Tryptamines", Journal of Labelled Compounds and Radiopharmaceuticals, vol. 51, No. 14, Nov. 1, 2008, pp. 423-429.

Cameron, et el., "Effects of N,N-Dimethyltryptamine on Rat Behaviors Relevant to Anxiety and Depression", ACS Chemical Neuroscience, 2018, 18 pages.

Celik, et al., "Binding of Serotonin to the Human Serotonin Transporter. Molecular Modeling and Experimental Validation", Mar. 2008.

Celik, et al., "Supplementary Information to Binding of Serotonin to the Human Serotonin Transporter. Molecular Modeling and Experimental Validation", Journal of the American Chemical Society, Mar. 2008, 14 pages.

Dunlap, et al., "Identification of Psychoplastogentic N,N-Dimethylaminoisotryptamine (isoDMT) Analogues through Structure—Activity Relationship Studies", Journal of Medicinal Chemistry, 2020, 14 pages.

Dyck, et al., "Effect of Deuterium Substitution on the Disposition of Intraperitoneal Tryptamine", Biochemical Pharmacology, vol. 35, No. 17, 1986, pp. 2893-2896.

Gaujac, et al., Investigations into the polymorphic properties of N,N-dimethyltryptamine by X-ray diffraction and differential scanning calorimetry, Microchemical Journal, 2013, 26 pages, 2013.

Ghosal, et al., "Indole Bases of Desmodium Gyrans", Phytochemistry (Elsevier), vol. 11, No. 5, 1972, 2 pages.

Grina, et al., "Old and New Alkaloids From Zanthoxylum Arborescens", Journal of Organic Chemistry, vol. 47, No. 13, 1982, pp. 2648-2651.

Halberstadt, et al., "Behavorial effects of x,x,B,B-tetradeutero-5-MeO-DMT in rats: comparison with 5-MeO-DMT administered in combination with a monoamine oxidase inhibitor", Psychopharmacology, Jan. 6, 2012.

Ibrahim, et al., "Marine inspired 2-(5-Halo-1H-indol-3-yl)-N,N-dimethylethanamines as Modulators of Serotonin Receptors: An Example Illustrating the Power of Bromine as Part of the Uniquely Marine Chemical Space", Marine drugs, 2017, 14 pages.

McIlhenny, et al., "Direct Analysis of Psychoactive Tryptamine and Harmala Alkaloids in the Amazonian Botanical Medicine Ayahuasca by Liquid", Journal of Chromatography A, vol. 1216, No. 51, 2009, 9 pages.

Morris, et al., "Indolealkylamine Metabolism: Synthesis of Deuterated Indolealkylamines as Metabolic Probes", Journal of Labelled Compounds and Radiopharmaceuticals, John Wiley & Sons Ltd., vol. 33, No. 6, 1993, pp. 455-465.

Queiroz, et al., "Chemical Composition of the Ark of Tetrapterys Mucronate and Identification of Acetrylcholinesterase Inhibitory Constituents", Journal of Natural Products, vol. 77, No. 3, 2014, 7 pages.

Riga, et al., The serotonin hallucinogen 5-MeO-DMT alters cortico-thalamic activity in freely moving mice: Regionally-selective incolovement of 5-HT1A and 5-HT2A receptors, Neuropharmacology, 2017, 12 pages.

Sard, et al., "SAR of psilocybin analogs: Discovery of a selective 5-HT2c agonist", Bioorganic & Medicinal Chemistry Letters 15, 2005, 5 pages.

Servillo, et al., "Citrus Genus Plants Contain N-Methylated Tryptamine Derivatives and Their 5-Hydroxylated Forms", Journal of Agricultural and Food Chemistry, vol. 61, No. 21, 2013, pp. 5156-5162.

Strassman, et al., "Dose-Response Study of N, N-Dimethyltryptamine in Humans: II. Subjective Effects and Preliminary Results of a New Rating Scale", Archives of General Psychiatry, Chicago, IL, Feb. 1994, 18 pages.

Tearavarich, et al., "Microwave-Accelerated Preparation and Analytical Characterization of 5-ethoxy-N,N-dialkyl-[α,α,β,β-H(4) ]- and [α,α,β,β-D(4) ]-tryptamines", Drug Testing and Analysis, vol. 3, No. 9, Dec. 2010, pp. 597-608.

Timmins, Graham S "Expert Opin ther Pat.", HHS Public Access, Oct. 2014, 19 Pages.

Walker, et al., "Gas Chromatographic-Mass Spectrometric Isotope Dilution Assay for N,N-Dimethyltryptamine in Human Plasma", Biochemical Medicine, vol. 8, Aug. 1972, pp. 105-113.

Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.

Rands et al.. Unpublished U.S. Appl. No. 17/616,345, filed Dec. 3, 2021.

Rands et al., Unpublished U.S. Appl. No. 17/574,424, filed Jan. 12, 2022.

Rands et al., Unpublished U.S. Appl. No. 17/680,411, filed Feb. 25, 2022.

Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.

Blair et al., "Effect of Ring Fluorination on the Pharmacology of Hallucinogenic Tryptamines", J Med. Chem., vol. 43, pp. 4701-4710. 2000.

Dunlap et al., "Reaction of N,N-Dimethyltryptamine with Dichloromethane Under Common Experimental Conditions", ACS Omega, vol. 3, pp. 4968-4973. 2018.

Tombari et al., "Ex Vivo Analysis of Tryptophan Metabolism Using 19F NMR", ACS Chem. Biol., vol. 14, pp. 1866-1873. 2019.

Yingxiang, "Drug Synthesis Reactions", (New World Era, 2nd edition), Beijing: China Press of Traditional Chinese Medicine, Aug. 2017, p. 134.

Chemieliva Pharmaceutical Produc, "Supplementary Disclosures", Chemieliva Pharmaceutical Product List, Order No. Cat CC0034141 Jan. 28, 2021.

Chemieliva Pharmaceutical Produc, "Supplementary Disclosures", Chemieliva Pharmaceutical Product List, Order No. Cat CC0034145 Jan. 28, 2021.

Reiff et al., "Psychedelics and Psychedelic-Assisted Psychotherapy", Am J. Psychiatry, 177:5, pp. 391-410. May 2020.

* cited by examiner

5-METHOXY-N,N-DIMETHYLTRYPTAMINE CRYSTALLINE FORMS

BACKGROUND

A method of producing a crystalline form of N,N-dimethyltryptamine fumarate (DMT fumarate) from DMT is disclosed in WO 2021/089873. This method comprises heating a solution of DMT and fumaric acid in ethanol at temperatures of 70° C. to 100° C. before cooling to 0° C. and subsequently collecting the crystalline DMT fumarate by filtration. The crystalline DMT fumarate, as well as its deuterated analogues have one Powder X-Ray Diffraction (PXRD) pattern.

Attempts to produce a crystalline form of 5-methoxy-N,N-dimethyltryptamine fumarate (5-MeO-DMT fumarate) or its deuterated analogues by the method of WO 2021/089873 have been less successful. A solution of 5-MeO-DMT and fumaric acid was not obtained, even at the high temperatures used. As a compromise, the suspension was cooled so that solid 5-MeO-DMT fumarate may be collected.

Thus, there is a need in the art for an alternative method to produce a crystalline fumarate salt of a 5-MeO-DMT compound. The present invention addresses this need. Surprisingly, the low temperature (about 15° C. to about 75° C.) method of the present invention provides crystalline fumarate salts of a 5-MeO-DMT compound of formula I in excellent yield.

It is known in the art that a different polymorph pattern would not be expected as a result of deuteration. As DMT fumarate and its deuterated analogues are known to exist as a single polymorph, it would be expected that 5-MeO-DMT fumarate and its deuterated analogues would behave in a similar way. Surprisingly, as demonstrated herein, 5-MeO-DMT fumarate and its deuterated analogues exist as at least three distinct polymorphs.

SUMMARY

Described herein are crystalline fumarate salts having a Formula I, pharmaceutical formulations comprising the same, methods for their production, and uses thereof, Formula I comprising:

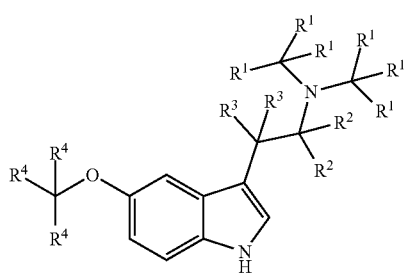

I wherein each $R^1$ is independently selected from protium and deuterium; each $R^2$ is independently selected from protium and deuterium; each $R^3$ is independently selected from protium and deuterium; and each $R^4$ is independently selected from protium and deuterium; and wherein the compound has a PXRD pattern comprising characteristic peaks at 19.2±0.2 and 24.7±0.2 degrees 2-theta.

Further aspects and embodiments of the present invention will be evident from the discussion that follows below.

DETAILED DESCRIPTION

Figure 1:
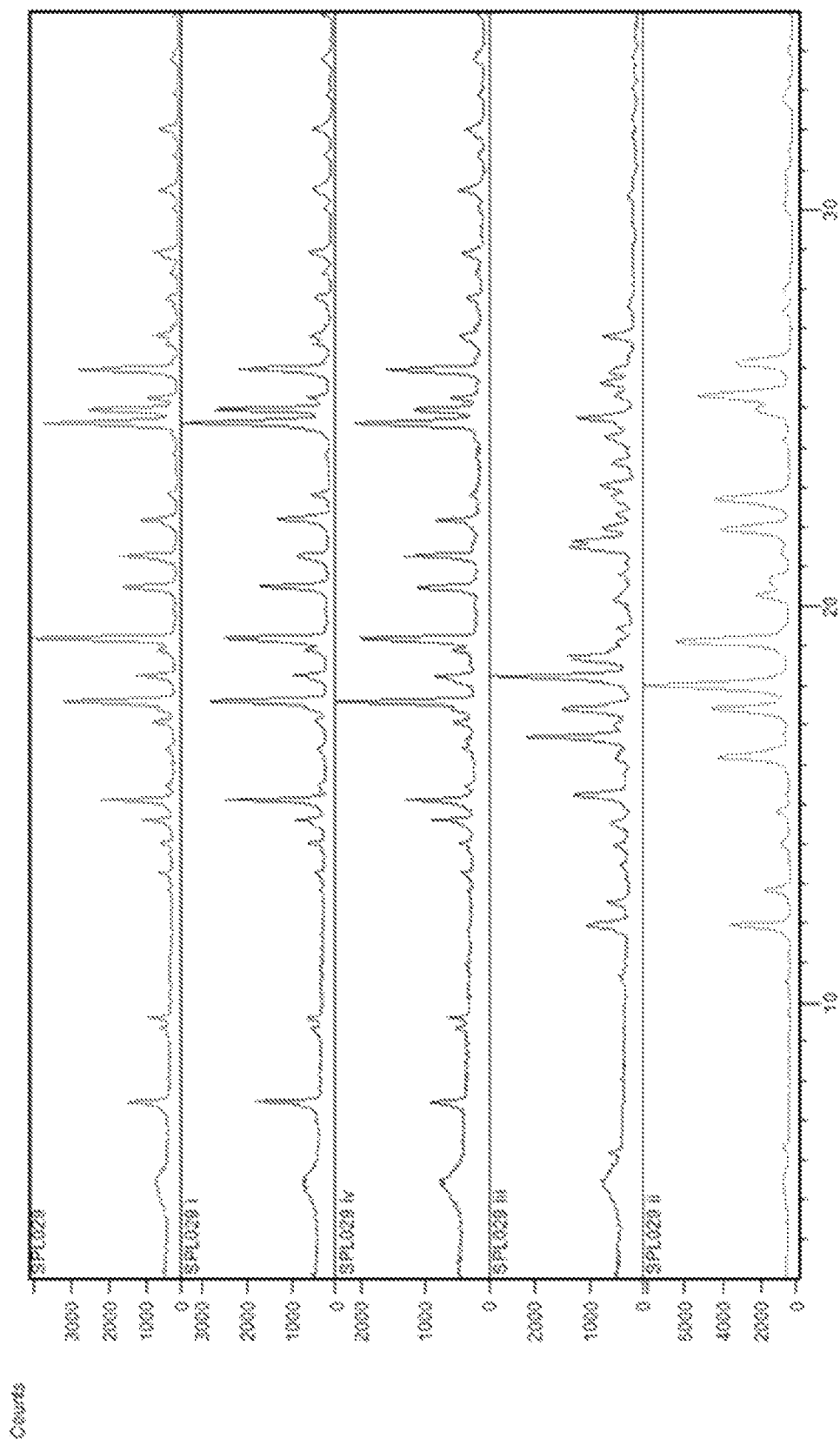
FIG. 1 is a Stacked Powder X-Ray Diffraction (PXRD) spectra of 5-methoxy-N,N-dimethyltryptamine fumarate (SPL029; D0), 5-methoxy-a-protio-b-deutero-N,N-dimethyltryptamine fumarate (SPL029i; D1), 5-methoxy-a,a-dideutero-N,N-dimethyltryptamine hemifumarate (SPL029ii; D2), 5-methoxy-N,N-dimethyl-$d_6$-tryptamine hemifumarate (SPL029iii; D6), and 5-methoxy-a,a-dideutero-N,N-dimethyl-$d_6$-tryptamine fumarate (SPL029iv; D8).
Figure 2:
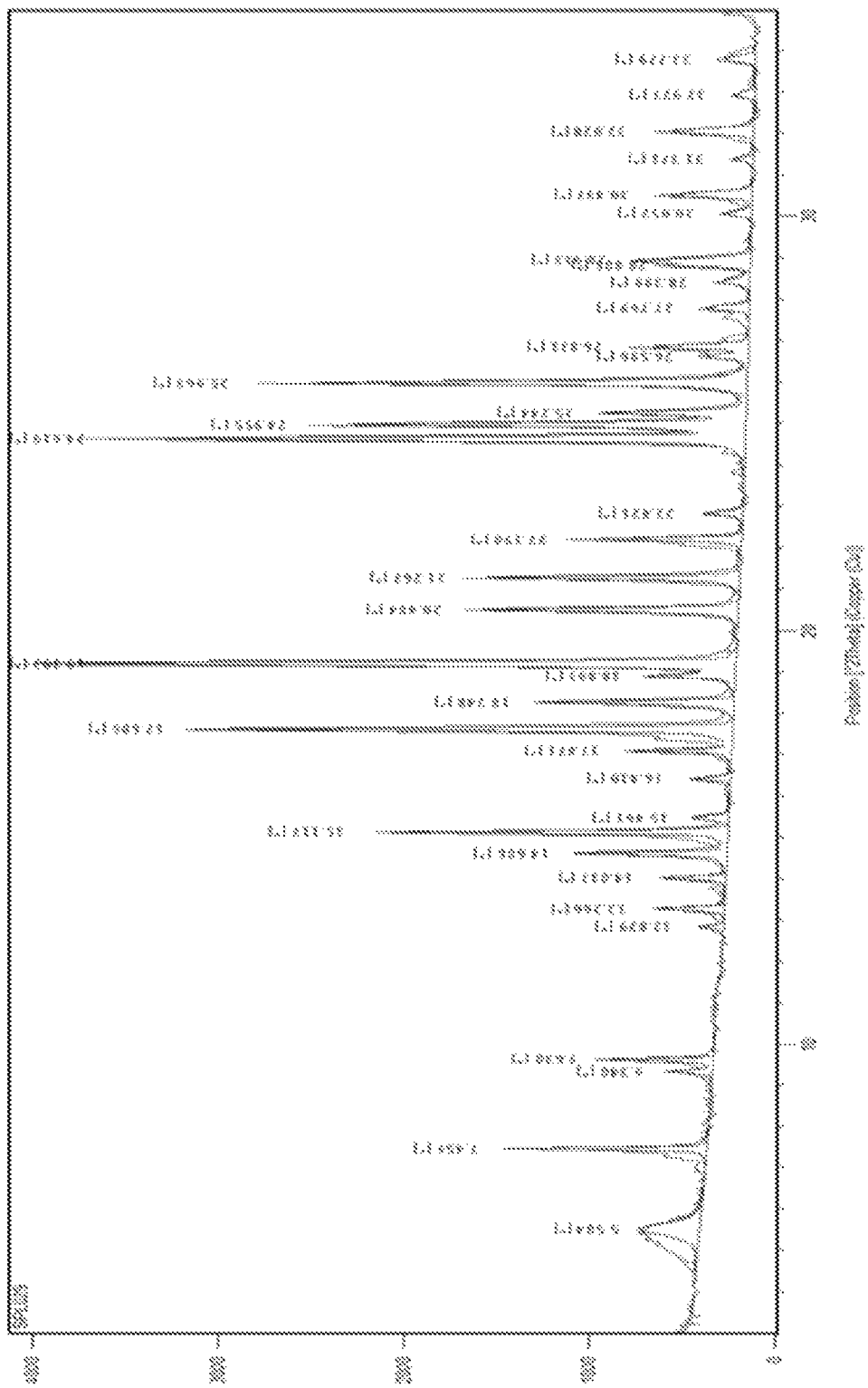
FIG. 2 is a PXRD spectrum of 5-methoxy-N,N-dimethyltryptamine fumarate (SPL029; D0).
Figure 3:
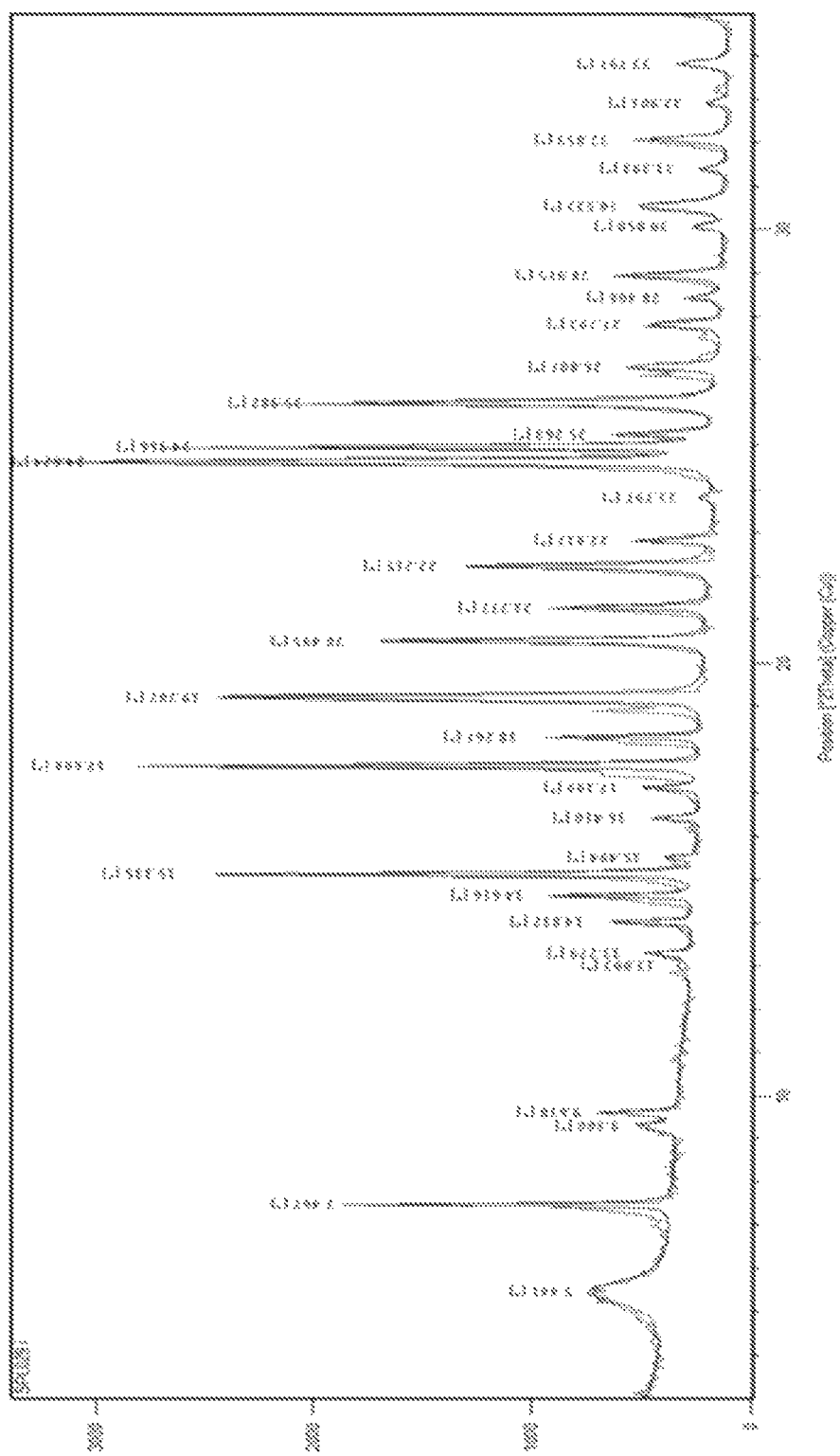
FIG. 3 is a PXRD spectrum of 5-methoxy-a-protio-b-deutero-N,N-dimethyltryptamine fumarate (SPL029i; D1).
Figure 4:
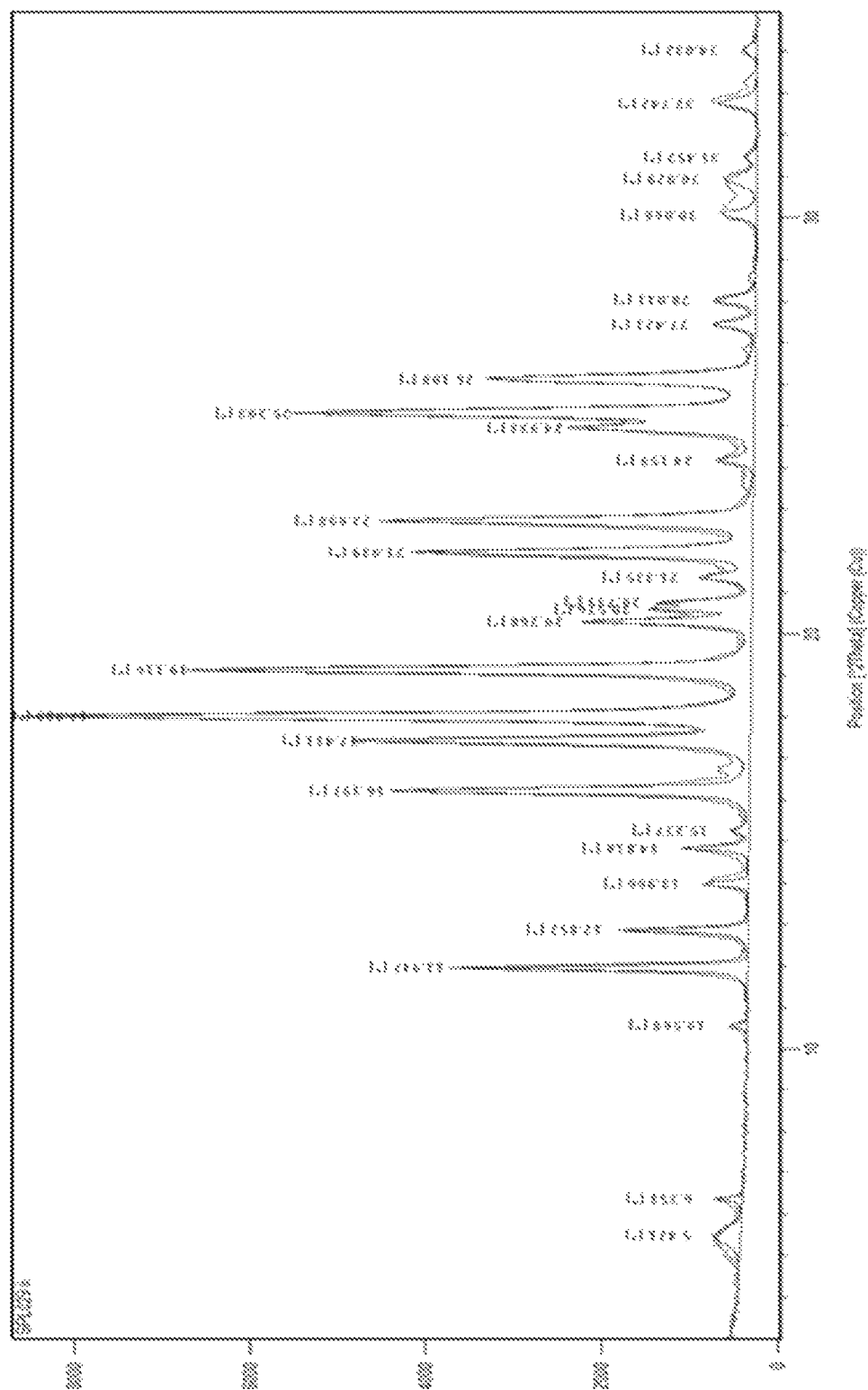
FIG. 4 is a PXRD spectrum of 5-methoxy-a,a-dideutero-N,N-dimethyltryptamine hemifumarate (SPL029ii; D2).
Figure 5:
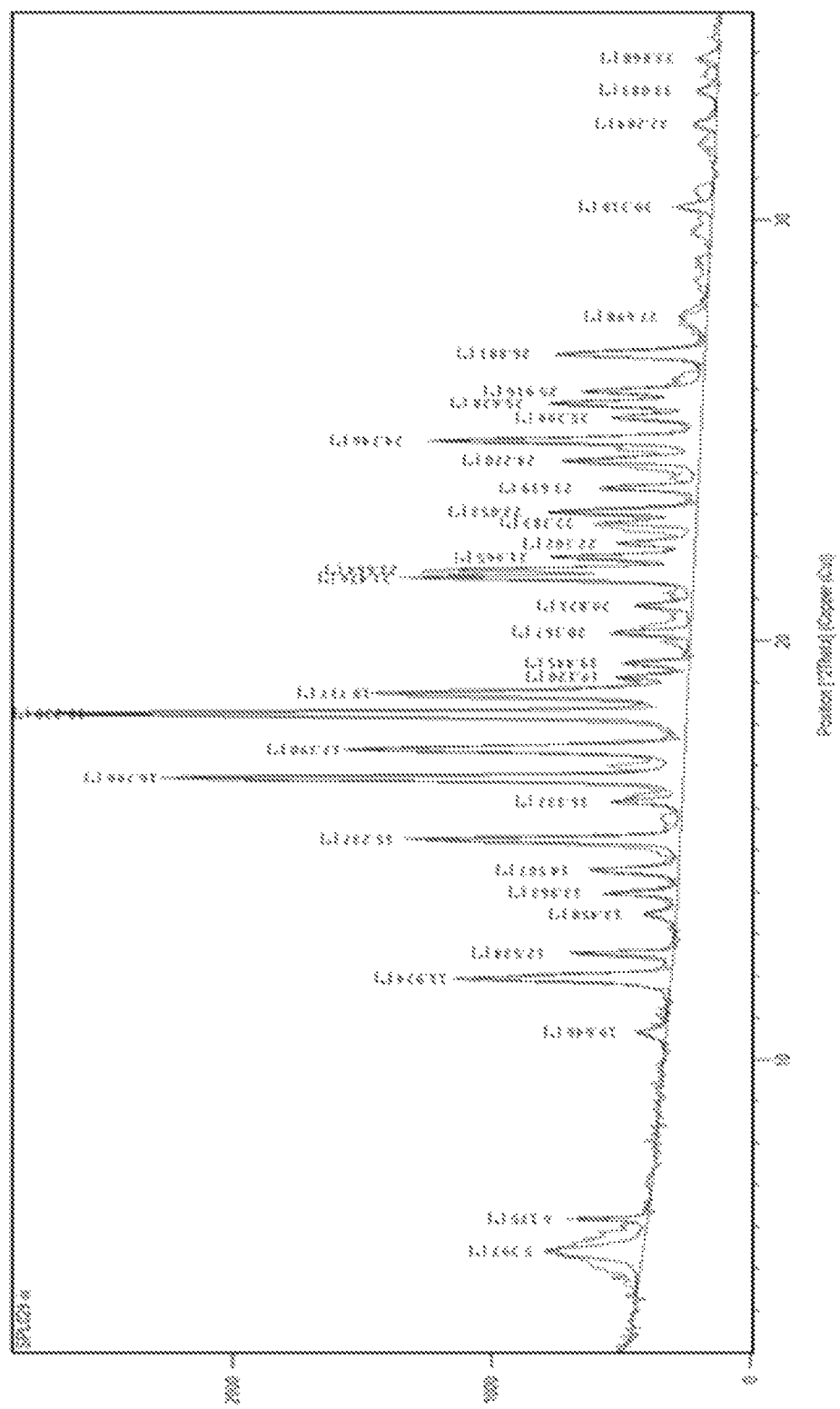
FIG. 5 is a PXRD spectrum of 5-methoxy-N,N-dimethyl-$d_6$-tryptamine hemifumarate (SPL029iii; D6).
Figure 6:
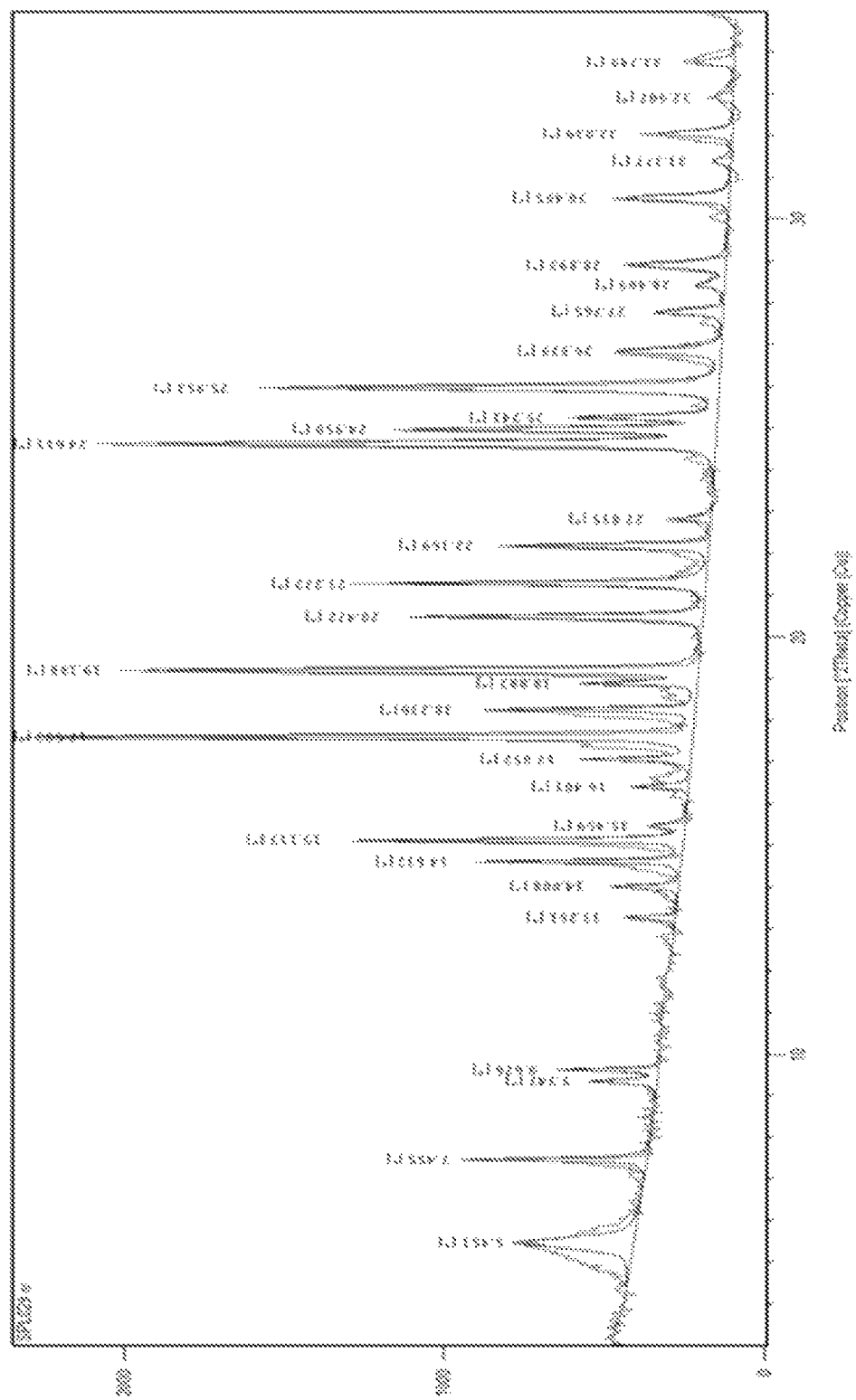
FIG. 6 is a PXRD spectrum of 5-methoxy-a,a-dideutero-N,N-dimethyl-$d_6$-tryptamine fumarate (SPL029iv; D8).
Figure 7:
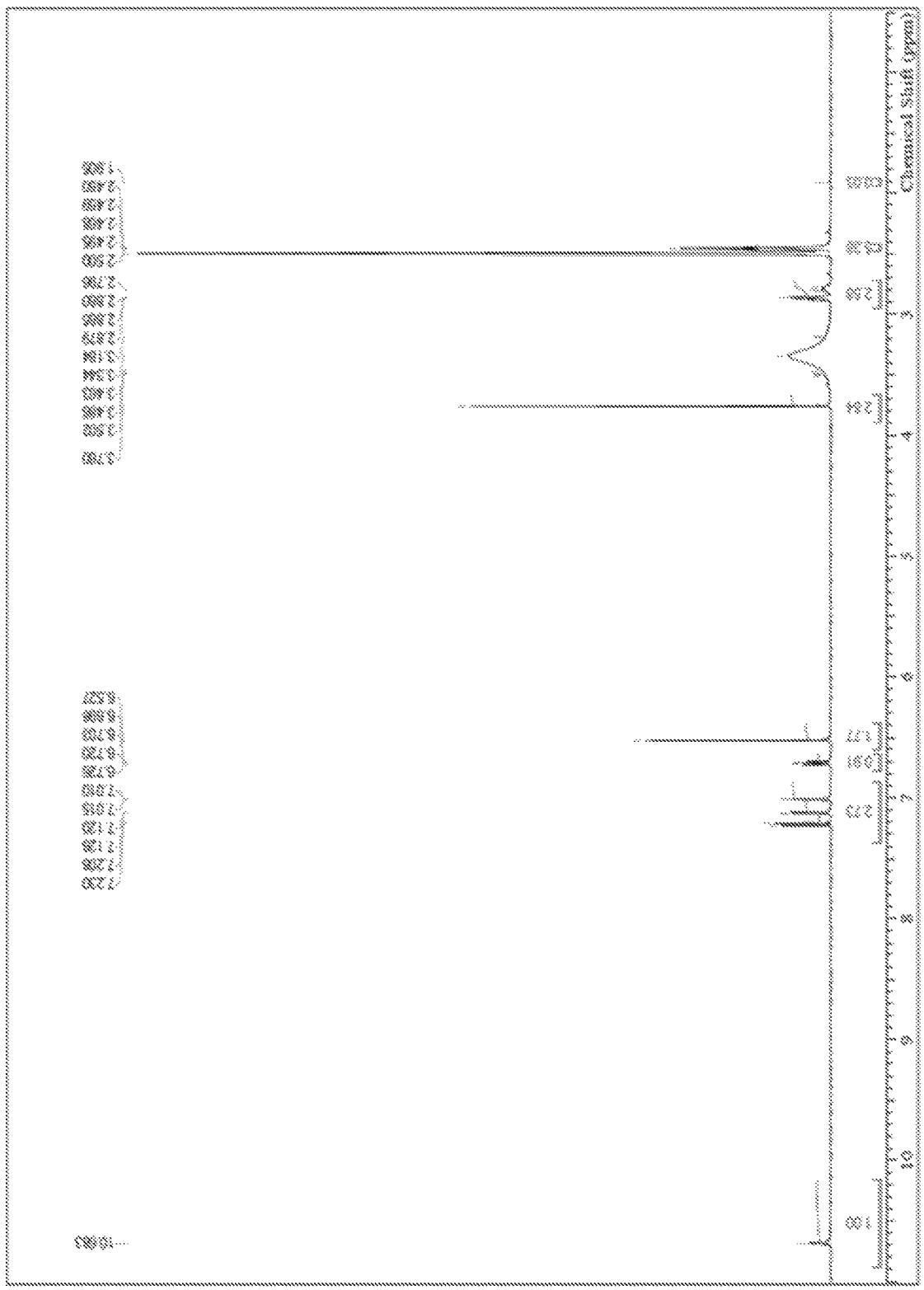
FIG. 7 is a $^1$H-NMR spectrum of 5-methoxy-a-protio-b-deutero-N,N-dimethyltryptamine fumarate (SPL029i; D1). $^1$H-NMR performed in deuterated dimethyl sulfoxide ($d_6$-DMSO).
Figure 8:
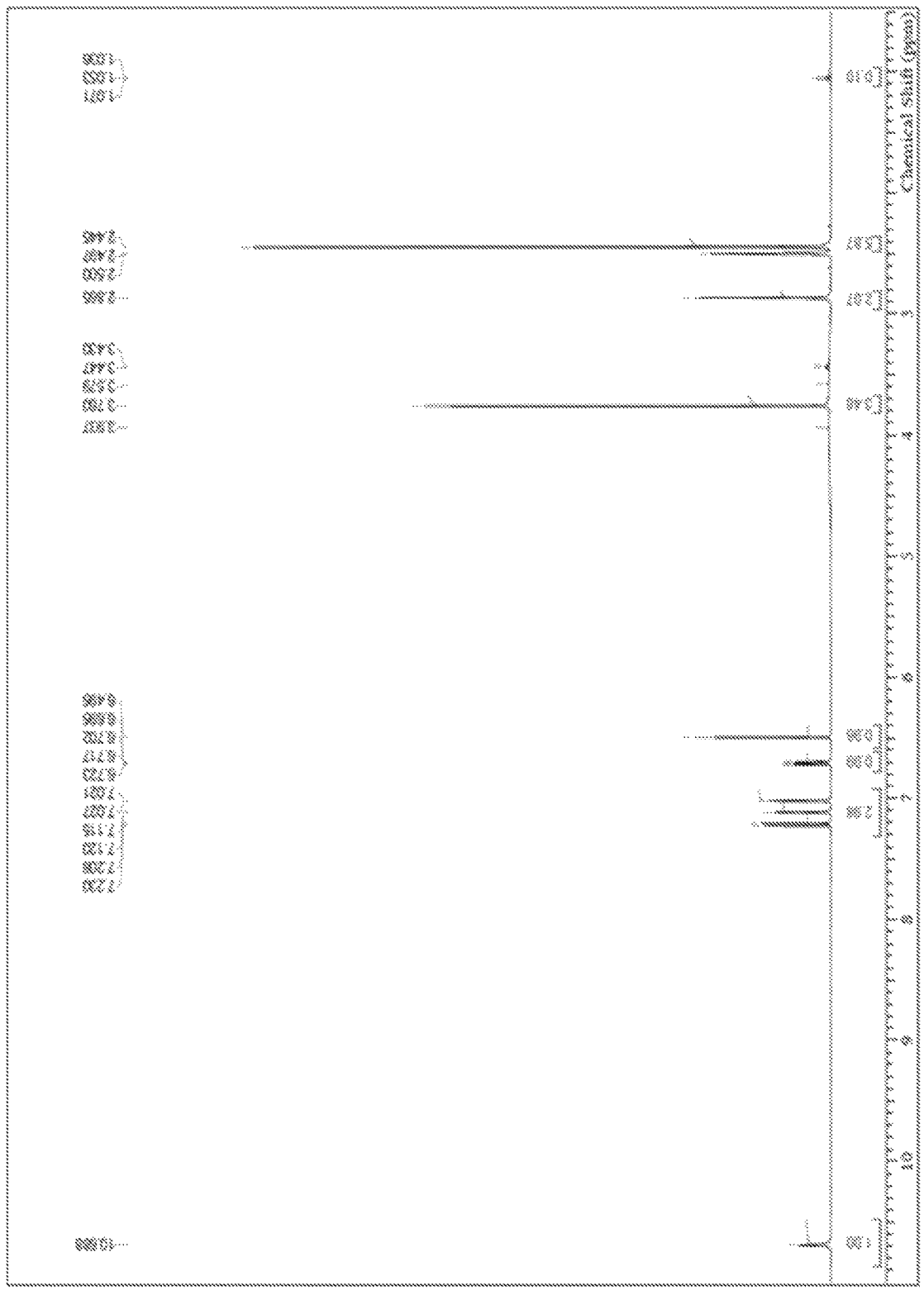
FIG. 8 is a $^1$H-NMR spectrum of 5-methoxy-a,a-dideutero-N,N-dimethyltryptamine hemifumarate (SPL029ii; D2). $^1$H-NMR performed in $d_6$-DMSO.
Figure 9:
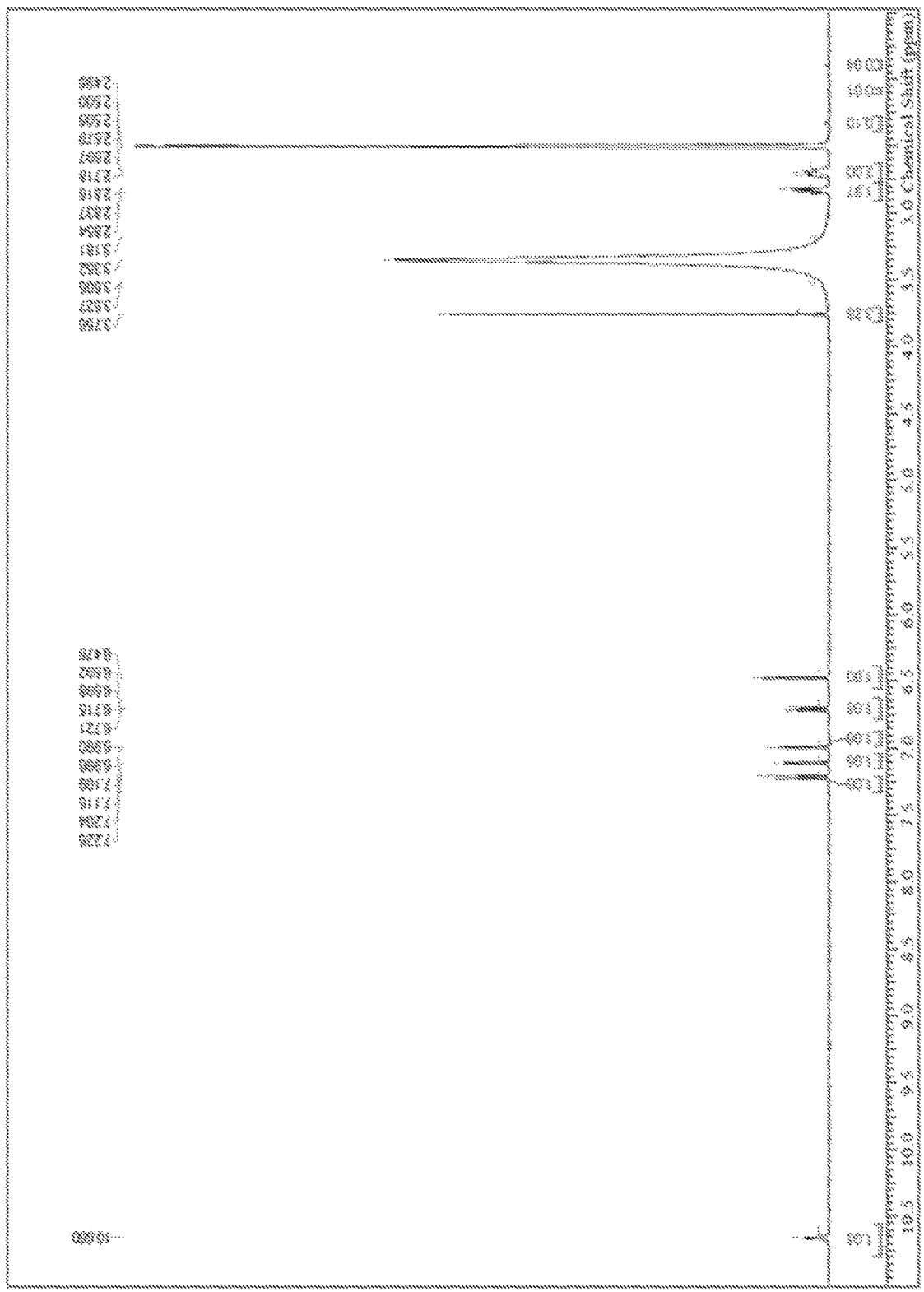
FIG. 9 is a $^1$H-NMR spectrum of 5-methoxy-N,N-dimethyl-$d_6$-tryptamine hemifumarate (SPL029iii; D6). $^1$H-NMR performed in $d_6$-DMSO.
Figure 10:
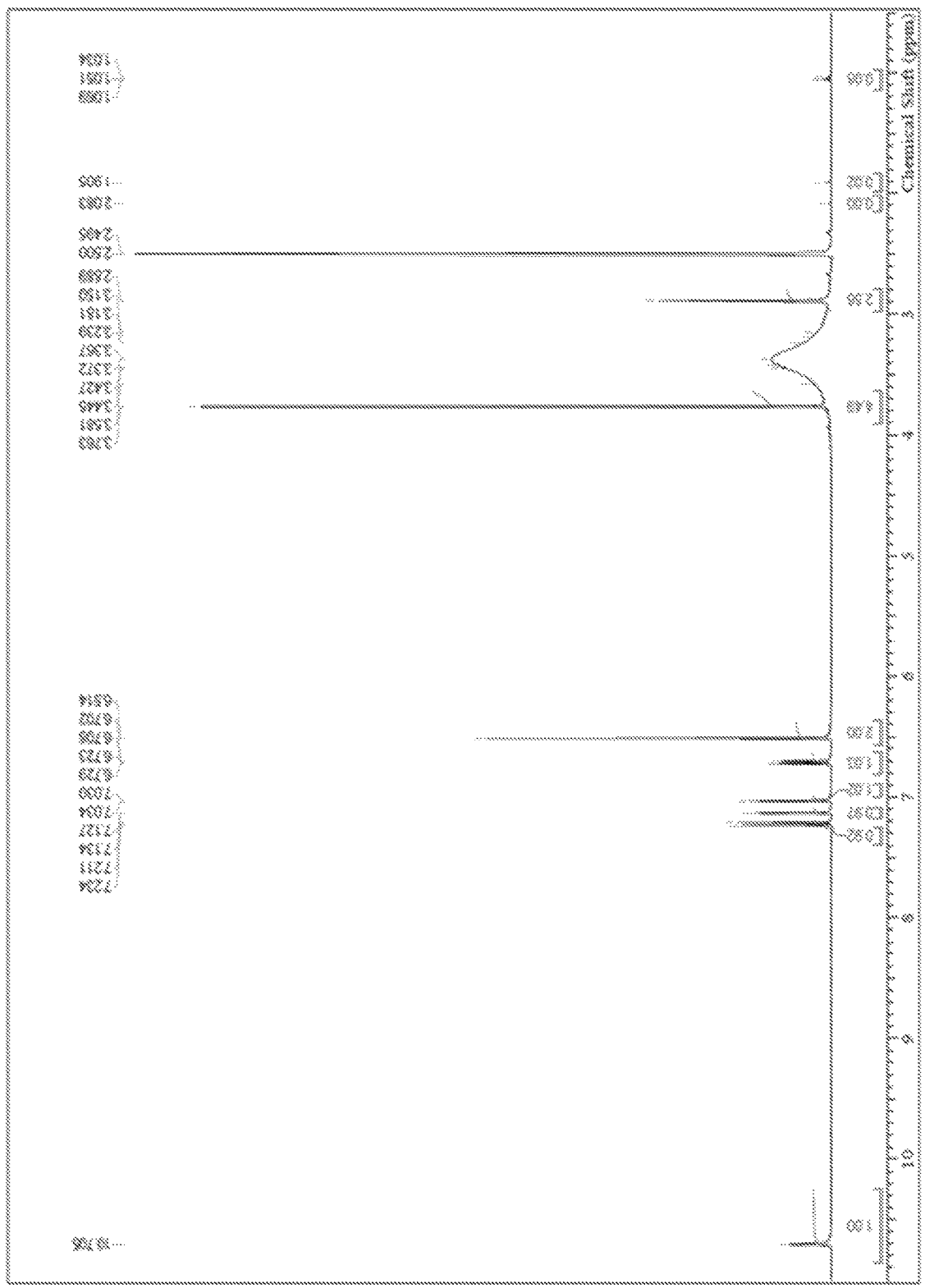
FIG. 10 is a $^1$H-NMR spectrum of 5-methoxy-a,a-dideutero-N,N-dimethyl-$d_6$-tryptamine fumarate (SPL029iv; D8). $^1$H-NMR performed in $d_6$-DMSO.

Throughout this specification, one or more aspects of the invention may be combined with one or more features described in the specification to define distinct embodiments of the invention.

In the discussion that follows, reference is made to a number of terms, which are to be understood to have the meanings provided below, unless a context expressly indicates to the contrary. The nomenclature used herein for defining compounds, in particular the compounds described herein, is intended to be in accordance with the rules of the International Union of Pure and Applied Chemistry (IUPAC) for chemical compounds, specifically the "IUPAC Compendium of Chemical Terminology (Gold Book)" (see A. D. Jenkins et al., Pure & Appl. Chem., 1996, 68, 2287-2311). For the avoidance of doubt, if a rule of the IUPAC organisation is contrary to a definition provided herein, the definition herein is to prevail.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "consisting" or variants thereof is to be understood to imply the inclusion of a stated element, integer or step, or group of elements, integers or steps, and the exclusion of any other element, integer or step or group of elements, integers or steps.

The term "about" herein, when qualifying a number or value, is used to refer to values that lie within ±5% of the value specified.

The term "hydrocarbyl" defines univalent groups derived from hydrocarbons by removal of a hydrogen atom from any carbon atom, wherein the term "hydrocarbon" refers to compounds consisting of hydrogen and carbon only. Where a hydrocarbyl is disclosed as optionally comprising one or more heteroatoms, any carbon or hydrogen atom on the hydrocarbyl may be substituted with a heteroatom or a functional group comprising a heteroatom, provided that valency is satisfied. One or more heteroatoms may be selected from the group consisting of nitrogen, sulfur and oxygen.

The term "alkyl" is well known in the art and defines univalent groups derived from alkanes by removal of a hydrogen atom from any carbon atom, wherein the term "alkane" is intended to define acyclic branched or unbranched hydrocarbons having the general formula $C_nH_{2n+2}$, wherein n is an integer≥1. $C_1$-$C_4$alkyl refers to any one selected from the group consisting of methyl, ethyl, n-propyl, iso-propyl, n-butyl, sec-butyl, isobutyl and tert-butyl.

The term "cycloalkyl" defines all univalent groups derived from cycloalkanes by removal of a hydrogen atom from a ring carbon atom. The term "cycloalkane" defines saturated monocyclic and polycyclic branched or unbranched hydrocarbons, where monocyclic cycloalkanes have the general formula $C_nH_{2n}$, wherein n is an integer 3. Typically, the cycloalkyl is a $C_5$-$C_6$cycloalkyl, such as cyclopentyl or cyclohexyl.

The term "alkylamino" refers to alkyl groups in which any one hydrogen atom is substituted with a primary (—NH$_2$), secondary (—NRH) or tertiary (—NR$_2$) amino groups, where R is, or each R is independently, a hydrocarbyl group. Typically, any one hydrogen atom is substituted with a tertiary amino group wherein each R is independently a $C_1$-$C_4$alkyl.

The term "treatment" defines the therapeutic treatment of a patient, in order to reduce or halt the rate of progression of a disorder, or to ameliorate or cure the disorder. Prophylaxis of a disorder as a result of treatment is also included. References to prophylaxis are intended herein not to require complete prevention of a disorder: its development may instead be hindered through treatment in accordance with the invention. Typically, treatment is not prophylactic, and the formulation is administered to a patient having a diagnosed or suspected disorder. As used herein, the term 'patient' preferably refers to a mammal. Typically the mammal is a human, but may also refer to a domestic mammal. The term does not encompass laboratory mammals.

Psychedelic-assisted psychotherapy means the treatment of a mental disorder by psychological means, which are enhanced by one or more protocols in which a patient is subjected to a psychedelic experience. A psychedelic experience is characterized by the striking perception of aspects of one's mind previously unknown, and may include one or more changes of perception with respect to hallucinations, synesthesia, altered states of awareness or focused consciousness, variation in thought patterns, trance or hypnotic states, and mystical states. The crystalline fumarate salt of the 5-methoxy-N,N-dimethyltryptamine compound of Formula I may be used in psychedelic-assisted psychotherapy.

As is understood in the art, psychiatric or neurological disorders are disorders which may be associated with one or more cognitive impairment. As used herein, the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric or neurological disorders referred to herein are provided in the Diagnostic and Statistical Manual of Mental Disorders, Fifth Edition, (DSM-5).

5-methoxy-N,N-dimethyltryptamine (5-MeO-DMT) is a short-acting psychoactive indolealkylamine found endogenously in the bufotoxin venom of the Colorado River toad (T. Lyttle, D. Goldstein and J. Gartz, J. Psychoact. Drugs, 1996, 28, 3, 267-290; A. T. Weil and W. Davis, J. Ethnopharmacol., 1994, 41, 1-2, 1-8), and in a variety of plant species including virola resin, peregrina seeds, and dictyoloma incanescens (; C. M. Torres and D. B. Repke, Anadenanthera: Visionary Plant of Ancient South America, 2006, The Haworth Herbal Press, Oxford).

As a structural analogue of serotonin, 5-MeO-DMT has affinity for the 5HT1A and 5HT2A receptor pathways, with particularly high affinity for 5HT1A, and also activates 5HT2A, 5HT3A, 5HT5, 5HT6 and 5HT7 receptors (A. L. Halberstadt and D. E. Nichols, Handbook of Behavioral Neuroscience, 2010, 21, 621-636; M. C. McBride, J. Psychoactive Drugs, 2000, 32, 3, 321-331). To a lesser degree, 5-MeO-DMT also activates the D1, D3, and alpha-2 receptors (T. S. Ray, PLOS One, 2010, 5, 2, e9019), and is a ligand for σ1 receptors (A. Szabo et al., PLOS One, 2014, 9, 8, e106533).

In an epidemiological study of over 500 individuals who have ingested 5-MeO-DMT in different forms in an uncontrolled setting, a high number of users reported therapeutic effects attributed to its use (A. K. Davis et al., J. Psychopharmacol., 2018, 32, 7, 779-792). Participants described as having psychiatric diagnoses indicated that their symptoms improved following 5-MeO-DMT use, including post-traumatic stress disorder (79%), depression (77%), and anxiety (69%). These responders reported infrequent use (<once/year), and not more than four times in their lifetime. Additionally, 5-MeO-DMT reportedly demonstrated a safe profile, as evidenced by the low intensity of challenging experiences (e.g., fear, anxiety) and low addiction liability (i.e., very low rates of craving, or legal, medical, psychiatric treatment associated with consumption).

Thus, 5-MeO-DMT and its deuterated analogues have therapeutic potential for treating psychiatric or neurological disorders in a patient.

As used herein the term 'obsessive-compulsive disorder' (OCD) is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically, OCD manifests as one or more obsessions, which drive adoption of a compulsion. For example, an obsession with germs may drive a compulsion to clean or an obsession with food may drive a compulsion to overeat, eat too little or throw up after eating (i.e. an obsession with food may manifest itself as an eating disorder). A compulsion can either be overt and observable by others, such as checking that a door is locked, or a covert mental act that cannot be observed, such as repeating a certain phrase in one's mind.

Herein, the term "eating disorder" includes anorexia nervosa, bulimia and binge eating disorder (BED). The symptoms of anorexia nervosa include eating too little and/or exercising too much in order to keep weight as low as possible. The symptoms of bulimia include eating a lot of food in a very short amount of time (i.e. binging) and then being deliberately sick, using laxatives, eating too little and/or exercising too much to prevent weight gain. The symptoms of BED include regularly eating large portions of food until uncomfortably full, and consequently feeling upset or guilty.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:
- depressed mood, such as feeling sad, empty or tearful (in children and teens, depressed mood can appear as constant irritability);
- significantly reduced interest or feeling no pleasure in all or most activities;
- significant weight loss when not dieting, weight gain, or decrease or increase in appetite (in children, failure to gain weight as expected);
- insomnia or increased desire to sleep;
- either restlessness or slowed behaviour that can be observed by others;
- fatigue or loss of energy;
- feelings of worthlessness, or excessive or inappropriate guilt;
- trouble making decisions, or trouble thinking or concentrating;
- recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
A. has depressed mood for most the time almost every day for at least two years. Children and adolescents may have irritable mood, and the time frame is at least one year.
B. While depressed, a person experiences at least two of the following symptoms:
  Either overeating or lack of appetite.
  Sleeping too much or having difficulty sleeping.
  Fatigue, lack of energy.
  Poor self-esteem.
  Difficulty with concentration or decision-making.

As used herein the term 'treatment resistant major depressive disorder' describes MDD that fails to achieve an adequate response to an adequate treatment with standard of care therapy.

As used herein, 'bipolar disorder', also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein, the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering a from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein, the term "post-partum depression" (PPD, also known as postnatal depression) is a form of depression experienced by either parent of a newborn baby. Symptoms typically develop within 4 weeks of delivery of the baby and often include extreme sadness, fatigue, anxiety, loss of interest or pleasure in hobbies and activities, irritability, and changes in sleeping or eating patterns.

As used herein, the term 'substance abuse' means a patterned use of a drug in which the user consumes the substance in amounts or with methods that are harmful to themselves or others.

As used herein, the term 'an avolition disorder' refers to a disorder that includes as a symptom the decrease in motivation to initiate and perform self-directed purposeful activities.

For the avoidance of doubt, where a reagent is expressed herein as a number of equivalents, this is with respect to the molar equivalents of the compound of formula III, formula II or formula I for reagents in stage 1, stage 2 or stage 3, respectively.

It is to be understood that "LiAl$^x$H$_4$" means the reducing agent (an agent capable of decreasing the oxidation level of an organic compound) lithium aluminium hydride when x is 1, so $^x$H is protium (hydrogen with atomic mass of 1), or lithium aluminium deuteride when x is 2, so $^x$H is deuterium (hydrogen with atomic mass of 2). According to some embodiments, therefore, "LiAl$^x$H$_4$" means LiAlH$_4$ and/or LiAlD$_4$. According to particular embodiments, mixtures of between 2% and 98% lithium aluminium hydride or between 2% and 98% lithium aluminium deuteride may be employed. Stage 2 of the method of the invention comprises reacting the compound of formula II with LiAlH$_4$ and/or LiAlD$_4$, i.e., LiAlH$_4$, LiAlD$_4$ or mixtures of the two may be reacted with the compound of formula II.

The term "coupling agent" refers to an agent which facilitates the chemical reaction between an amine and a carboxylic acid. In some embodiments, the two or more coupling agents comprise a carboxylic acid activating agent, i.e. an agent which reacts with the carboxylic acid moiety of formula I to produce a compound comprising an activated moiety derived from the original carboxylic acid moiety that is more likely to react with an amine than the original carboxylic acid moiety.

An additive coupling agent (also referred to herein as an "additive") is an agent which enhances the reactivity of a coupling agent. In some embodiments, the additive is a compound capable of reacting with the product of the reaction of formula I and the coupling agent (the product being a compound comprising an activated moiety) to produce a compound comprising an even more activated moiety that is more likely to react with an amine than the original activated moiety.

High-performance liquid chromatography (HPLC), is a technique in analytical chemistry used to separate, identify, and quantify each component in a mixture. For a review of HPLC, see A. M. Sabir et al., Int. Res. J. Pharm., 2013, 4, 4, 39-46.

Solvents referred to herein include MeCN (acetonitrile), DCM (dichloromethane), acetone, IPA (isopropyl alcohol), iPrOAc (isopropyl acetate), TBME (t-butyl methyl ether), THF (tetrahydrofuran), 2-MeTHF (2-methyl tetrahydrofuran), EtOAc (ethyl acetate), ethanol and toluene. As used herein, the term ether solvent means a solvent containing an alkyl-O-alkyl moiety, wherein the two alkyl components may be connected. Ether solvents include diethyl ether, TBME, THF and 2-MeTHF.

A drying agent is a chemical used to remove water from an organic compound that is in solution. Examples of drying agents include calcium chloride, magnesium sulphate, and sodium sulphate. Drying agents described herein are typically magnesium sulphate.

Aqueous basic solution means a mild base suitable for workup, for example a 10% potassium carbonate solution.

In a first aspect, the invention provides a crystalline fumarate salt of a 5-methoxy-N,N-dimethyltryptamine compound of Formula I having a PXRD pattern comprising characteristic peaks at 19.2±0.2 and 24.7±0.2 degrees 2-theta:

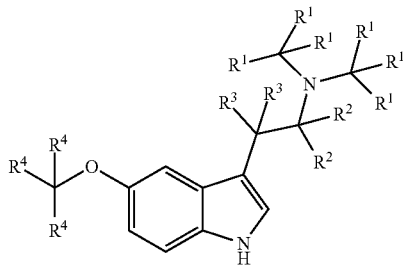

wherein each R$^1$ is independently selected from protium and deuterium, each R$^2$ is independently selected from protium and deuterium, each R$^3$ is independently selected from protium and deuterium, and each R$^4$ is independently selected from protium and deuterium.

For the avoidance of doubt, "fumarate salt" used herein refers to a fumarate salt or a hemifumarate salt. A hemifumarate salt is a salt having a 2:1 ratio of compound of formula I to fumarate. A fumarate salt is a salt having a 1:1 ratio of compound of formula I to fumarate.

The crystalline fumarate salt of a 5-methoxy-N,N-dimethyltryptamine compound of Formula I may have a PXRD pattern further comprising characteristic peaks at 18.2±0.2 degrees 2-theta.

Preferably, the crystalline fumarate salt of the 5-methoxy-N,N-dimethyltryptamine compound of formula I may be white or colourless.

In some embodiments, one or more R$^1$ may be deuterium. In some embodiments, each R$^1$ may be deuterium. In some embodiments, one or more R$^2$ may be deuterium. In some embodiments, each R$^2$ may be deuterium. In some embodiments, each R$^3$ may be protium. In some embodiments, each R$^4$ may be protium.

In a preferred embodiment, each R$^1$ is protium, each R$^2$ is protium, each R$^3$ is protium, and each R$^4$ is protium. In this embodiment, the crystalline fumarate salt of the 5-methoxy-N,N-dimethyltryptamine compound is in crystalline polymorph pattern A. In this embodiment, the crystalline fumarate salt of the 5-methoxy-N,N-dimethyltryptamine compound is a fumarate salt.

In a preferred embodiment, each R$^1$ is protium, one R$^2$ is protium and one R$^2$ is deuterium, each R$^3$ is protium, and each R$^4$ is protium. In this embodiment, the crystalline fumarate salt of the 5-methoxy-N,N-dimethyltryptamine compound is in crystalline polymorph pattern A. In this embodiment, the crystalline fumarate salt of the 5-methoxy-N,N-dimethyltryptamine compound is a fumarate salt.

In a preferred embodiment, each R$^1$ is protium, each R$^2$ is deuterium, each R$^3$ is protium, and each R$^4$ is protium. In this embodiment, the crystalline fumarate salt of the 5-methoxy-N,N-dimethyltryptamine compound is in crystalline polymorph pattern B. In this embodiment, the crystalline fumarate salt of the 5-methoxy-N,N-dimethyltryptamine compound is a hemifumarate salt.

In a preferred embodiment, each R$^1$ is deuterium, each R$^2$ is protium, each R$^3$ is protium, and each R$^4$ is protium. In this embodiment, the crystalline fumarate salt of the 5-methoxy-N,N-dimethyltryptamine compound is in crystalline polymorph pattern C. In this embodiment, the crystalline fumarate salt of the 5-methoxy-N,N-dimethyltryptamine compound is a hemifumarate salt.

In a preferred embodiment, each R$^1$ is deuterium, each R$^2$ is deuterium, each R$^3$ is protium, and each R$^4$ is protium. In this embodiment, the crystalline fumarate salt of the 5-methoxy-N,N-dimethyltryptamine compound is in crystalline polymorph pattern A. In this embodiment, the crystalline fumarate salt of the 5-methoxy-N,N-dimethyltryptamine compound is a fumarate salt.

Polymorph pattern A may be the thermodynamically favoured polymorph form of crystalline fumarate salts of the 5-methoxy-N,N-dimethyltryptamine compound. Crystalline fumarate salts of the 5-methoxy-N,N-dimethyltryptamine compound having polymorph pattern A display very good stability. In addition, crystalline fumarate salts of the 5-methoxy-N,N-dimethyltryptamine compound having polymorph pattern A have good stability as compared to crystalline fumarate salts of the 5-methoxy-N,N-dimethyltryptamine compound having polymorph patterns B or C.

Crystalline polymorph pattern A has a PXRD pattern comprising characteristic peaks at 7.5±0.2, 20.5±0.2, 22.2±0.2 and 25.0±0.2 degrees 2-theta. Crystalline polymorph pattern A has a PXRD pattern further comprising characteristic peaks at 15.1±0.2, 17.6±0.2, 18.3±0.2, 19.2±0.2, 21.3±0.2, 24.6±0.2, and 26.0±0.2 degrees 2-theta.

Crystalline polymorph pattern B has a PXRD pattern comprising characteristic peaks at 11.9±0.2 and 16.2±0.2 degrees 2-theta. Crystalline polymorph pattern B has a PXRD pattern further comprising characteristic peaks at 12.9±0.2, 17.4±0.2, 18.0±0.2, 19.1±0.2, 21.9±0.2, 22.7±0.2, 24.9±0.2, 25.3±0.2, and 26.1±0.2 degrees 2-theta.

Crystalline polymorph pattern C has a PXRD pattern comprising characteristic peaks at 11.9±0.2, 15.2±0.2 and 16.7±0.2 degrees 2-theta. Crystalline polymorph pattern C has a PXRD pattern further comprising characteristic peaks at 12.5±0.2, 15.2±0.2, 17.4±0.2, 18.2±0.2, 18.7±0.2, 21.5±0.2, 21.7±0.2, and 24.7±0.2 degrees 2-theta.

All of crystalline polymorph forms A, B and C have a diffraction pattern comprising characteristic peaks at 18.2±0.2, 19.2±0.2 and 24.7±0.2 degrees 2-theta.

In a second aspect, the present invention provides a method of producing a crystalline fumarate salt of a 5-methoxy-N,N-dimethyltryptamine compound of Formula I,

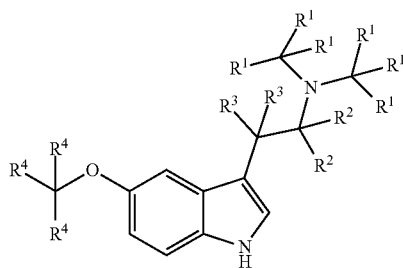

wherein each $R^1$ is independently selected from protium and deuterium, each $R^2$ is independently selected from protium and deuterium, each $R^3$ is independently selected from protium and deuterium, and each $R^4$ is independently selected from protium and deuterium, and wherein the method comprises the steps of:
a. Dissolving a freebase of the 5-methoxy-N,N-dimethyltryptamine compound in ethanol at a temperature of about 15° C. to about 75° C. to form an ethanolic solution of the 5-methoxy-N,N-dimethyltryptamine compound;
b. contacting the ethanolic solution of the 5-methoxy-N,N-dimethyltryptamine compound with fumaric acid to form a mixture;
c. stirring the mixture for between about 15 and about 45 minutes, optionally in the presence of seed crystals of the fumarate salt of the 5-methoxy-N,N-dimethyltryptamine compound;
d. cooling the mixture to between about 5° C. and about 0° C.; and
e. filtering the mixture to collect the crystalline fumarate salt of the 5-methoxy-N,N-dimethyltryptamine compound.

Preferably, the dissolving step a. is carried out at a temperature of about 25° C. to about 70° C., or about 35° C. to about 60° C., or about 40° C. to about 50° C., most preferably the dissolving step a. is carried out at a temperature of about 70° C. In embodiments, the dissolving step a. is carried out at a temperature of about 15° C. to about 25° C., or about 18° C. to about 21° C. Preferably, the freebase of the 5-methoxy-N,N-dimethyltryptamine compound is dissolved in between about 5 and about 20 volumes of ethanol.

Preferably, in the dissolving step a. the ethanol is stirred for between about 1 and about 30 minutes to form the ethanolic solution of the 5-methoxy-N,N-dimethyltryptamine compound. Preferably, the ethanol is stirred for between about 5 and about 25 minutes, or between about 10 and about 20 minutes.

Preferably, step b. is carried out at a temperature of about 15° C. to about 75° C., about 25° C. to about 65° C., or about 35° C. to about 55° C., or about 40° C. to about 50° C., most preferably, step b. is carried out at a temperature of about 70° C. In embodiments, step b. is carried out at a temperature of about 15° C. to about 25° C., or about 18° C. to about 21° C. Preferably, in step b. the ethanolic solution of the 5-methoxy-N,N-dimethyltryptamine compound is contacted with fumaric acid for between about 1 and about 30 minutes to form the mixture of the 5-methoxy-N,N-dimethyltryptamine compound and fumaric acid. Preferably, the ethanolic solution of the 5-methoxy-N,N-dimethyltryptamine compound is contacted with fumaric acid for between about 5 and about 25 minutes, or between about 10 and about 20 minutes. For the avoidance of doubt, the mixture comprises an ethanolic solution of the fumarate salt of the 5-methoxy-N,N-dimethyltryptamine compound of formula I.

Preferably, in step c. the mixture is stirred for between about 20 and about 40 minutes, between about 25 and about 35 minutes, or between about 25 and about 30 minutes. Preferably, in step c. the mixture is stirred at a temperature of about 15° C. to about 75° C., about 25° C. to about 65° C., or about 35° C. to about 55° C.

Preferably, the step c. is carried out in the presence of seed crystals of the fumarate salt of the 5-methoxy-N,N-dimethyltryptamine compound. When present, the seed crystals of the fumarate salt of the 5-methoxy-N,N-dimethyltryptamine compound may have a PXRD pattern comprising characteristic peaks at 19.2±0.2 and 24.7±0.2 degrees 2-theta. The seed crystals of the fumarate salt of the 5-methoxy-N,N-dimethyltryptamine compound may have a PXRD pattern comprising further characteristic peaks at 18.2±0.2 degrees 2-theta Preferably, the cooling step d. is carried out at a rate of about 1° C. to about 10° C. per hour, more preferably about 3° C. to about 8° C. per hour, most preferably about 5° C. per hour.

Optionally, the method of the second aspect may include a step f. following step e:

f. drying the crystalline fumarate salt of the 5-methoxy-N,N-dimethyltryptamine compound.

The method of the second aspect of the invention may provide a crystalline fumarate salt of the 5-methoxy-N,N-dimethyltryptamine compound according to the first aspect of the invention.

In a third aspect, the invention provides a crystalline fumarate salt of a 5-methoxy-N,N-dimethyltryptamine compound obtainable by the method of the second aspect.

For the avoidance of doubt, embodiments related to the crystalline fumarate salt of a 5-methoxy-N,N-dimethyltryptamine compound of formula I defined in the first aspect of the invention apply mutatis mutandis to the crystalline fumarate salt of a 5-methoxy-N,N-dimethyltryptamine compound of formula I of the second and third aspects.

Accordingly, in a fourth aspect, the invention provides a crystalline fumarate salt of a 5-methoxy-N,N-dimethyltryptamine compound as defined in the first or third aspects for use in a method of treating a psychiatric or neurological disorder in a patient. The psychiatric or neurological disorder may be selected from the group consisting of (i) an obsessive compulsive disorder, (ii) a depressive disorder, (iii) an anxiety disorder, (iv) substance abuse, and (v) an avolition disorder. Often the psychiatric or neurological disorder may be selected from the group consisting of major depressive disorder, treatment resistant major depressive disorder, post-partum depression, an obsessive compulsive disorder and an eating disorder such as a compulsive eating disorder. The depressive disorder may be major depressive disorder, treatment resistant major depressive disorder, or post-partum depression.

In a fifth aspect, the invention provides a method of treating a psychiatric or neurological disorder comprising administering to a patient in need thereof a crystalline fumarate salt of a 5-methoxy-N,N-dimethyltryptamine compound as defined in the first or third aspects. The psychiatric or neurological disorder may be any of those described in relation to the fourth aspect. For example, the disorder may be selected from the group consisting of major depressive disorder, treatment resistant major depressive disorder, post-partum depression, an obsessive compulsive disorder and an eating disorder such as a compulsive eating disorder.

In a sixth aspect, the invention provides a use of a fumarate salt of a 5-methoxy-N,N-dimethyltryptamine compound as defined in the first or third aspects for the manufacture of a medicament. In some embodiments, the medicament is for use in a method of treating a psychiatric or neurological disorder in a patient. The psychiatric or neurological disorder may be any of those described in relation to the fourth aspect.

For the avoidance of doubt, all embodiments related to the first aspect of the invention as defined herein apply mutatis mutandis to the fourth, fifth and sixth aspects.

As described above, in a second aspect the present invention provides a method of producing a crystalline fumarate salt of a 5-methoxy-N,N-dimethyltryptamine compound of Formula I,

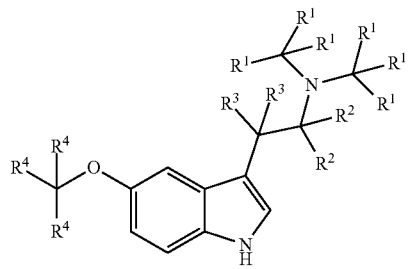

wherein each $R^1$ is independently selected from protium and deuterium, each $R^2$ is independently selected from protium and deuterium, each $R^3$ is independently selected from protium and deuterium, and each $R^4$ is independently selected from protium and deuterium, and wherein the method comprises the steps of:

a. Dissolving a freebase of the 5-methoxy-N,N-dimethyltryptamine compound in ethanol at a temperature of about 15° C. to about 75° C. to form an ethanolic solution of the 5-methoxy-N,N-dimethyltryptamine compound;

b. contacting the ethanolic solution of the 5-methoxy-N,N-dimethyltryptamine compound with fumaric acid to form a mixture;

c. stirring the mixture for between about 15 and about 45 minutes, optionally in the presence of seed crystals of the fumarate salt of the 5-methoxy-N,N-dimethyltryptamine compound;

d. cooling the mixture to between about 5° C. and about 0° C.; and e. filtering the mixture to collect the crystalline fumarate salt of the 5-methoxy-N,N-dimethyltryptamine compound.

'Stage 3' as used herein refers to the method of the second aspect.

Optionally, the method of the second aspect may include a step f. following step e:

f. drying the crystalline fumarate salt of the 5-methoxy-N,N-dimethyltryptamine compound.

In some embodiments, a ratio of fumaric acid:compound of formula I of 1:1 is used. Often, the ratio of fumaric acid:compound of formula I is 1:1.

As described herein, the steps of stage 3 are carried out in ethanol.

Preferably, the dissolving step a. is carried out at a temperature of about 25° C. to about 70° C., or about 35° C. to about 60° C., or about 40° C. to about 50° C., most preferably the dissolving step a. is carried out at a temperature of about 70° C. In embodiments, the dissolving step a. is carried out at a temperature of about 15° C. to about 25° C., or about 18° C. to about 21° C. Preferably, the freebase of the 5-methoxy-N,N-dimethyltryptamine compound is dissolved in between about 5 and about 20 volumes of ethanol, or between about 10 and about 15 volumes of ethanol.

Preferably, in the dissolving step a. the ethanol is stirred for between about 1 and about 30 minutes to form the ethanolic solution of the 5-methoxy-N,N-dimethyltryptamine compound. Preferably, the ethanol is stirred for between about 5 and about 25 minutes, or between about 10 and about 20 minutes.

Preferably, step b. is carried out at a temperature of about 15° C. to about 75° C., about 25° C. to about 65° C., or about 35° C. to about 55° C., or about 40° C. to about 50° C., most preferably, step b. is carried out at a temperature of about 70° C. In embodiments, step b. is carried out at a temperature of about 15° C. to about 25° C., or about 18° C. to about 21° C. Preferably, in step b. the ethanolic solution of the 5-methoxy-N,N-dimethyltryptamine compound is contacted with fumaric acid for between about 1 and about 30 minutes to form the mixture of the 5-methoxy-N,N-dimethyltryptamine compound and fumaric acid. Preferably, the ethanolic solution of the 5-methoxy-N,N-dimethyltryptamine compound is contacted with fumaric acid for between about 5 and about 25 minutes, or between about 10 and about 20 minutes. For the avoidance of doubt, the mixture comprises an ethanolic solution of the fumarate salt of the 5-methoxy-N,N-dimethyltryptamine compound of formula I.

Preferably, in step c. the mixture is stirred for between about 20 and about 40 minutes, between about 25 and about 35 minutes, or between about 25 and about 30 minutes. Preferably, in step c. the mixture is stirred at a temperature of about 15° C. to about 75° C., about 25° C. to about 65° C., or about 35° C. to about 55° C.

Preferably, the step c. is carried out in the presence of seed crystals of the fumarate salt of the 5-methoxy-N,N-dimethyltryptamine compound. When present, the seed crystals of the fumarate salt of the 5-methoxy-N,N-dimethyltryptamine compound may have a PXRD pattern comprising characteristic peaks at 19.2±0.2 and 24.7±0.2 degrees 2-theta. The seed crystals of the fumarate salt of the 5-methoxy-N,N-dimethyltryptamine compound may have a PXRD pattern comprising further characteristic peaks at 18.2±0.2 degrees 2-theta Preferably, the cooling step d. is carried out at a rate of about 1° C. to about 10° C. per hour, more preferably about 3° C. to about 8° C. per hour, most preferably about 5° C. per hour.

The crystalline fumarate salt of the 5-methoxy-N,N-dimethyltryptamine compound may be recrystallised. The skilled person is aware of techniques that are suitable for recrystallisation of a crystalline fumarate salt of the 5-methoxy-N,N-dimethyltryptamine compound. For example, the crystalline fumarate salt of the 5-methoxy-N,N-dimethyltryptamine compound of formula I may be dissolved in the minimum amount of solvent at a particular temperature (e.g. at ambient temperature (e.g. about 15 to about 25° C.) or at elevated temperatures where heat is applied to the solution) and the resultant solution cooled to encourage precipitation. Alternatively, or in addition, the volume of the solution may be reduced to encourage precipitation, e.g. by simple evaporation at ambient temperature and pressure. Alternatively, or in addition, an anti-solvent may be used (in which the crystalline fumarate salt of the 5-methoxy-N,N-dimethyltryptamine compound of formula I is less soluble than the solvent already present).

Isolated crystalline fumarate salts of the 5-methoxy-N,N-dimethyltryptamine compound of formula I are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer. In some embodiments, the crystalline fumarate salt of the 5-methoxy-N,N-dimethyltryptamine compound of formula I is stored in a solvent, for example dissolved in ethanol. In some embodiments, the compound of formula I is stored in a solvent for more than about 8 hours, typically more than about 12 hours.

Optionally, the freebase of the 5-methoxy-N,N-dimethyltryptamine compound of formula I may be prepared from a compound of formula II in 'Stage 2':

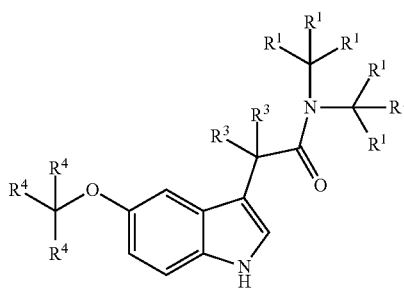

The compound of formula II may be prepared from a compound of formula III in 'Stage 1':

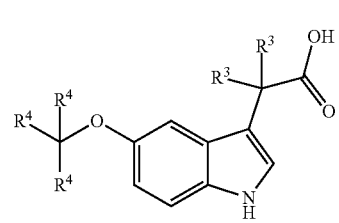

For the avoidance of doubt, the definitions of $R^1$, $R^3$ and $R^4$ in respect of compounds of formula I apply mutatis mutandis to compounds of formula II and III.

Stage 1 may comprise the steps of:
(i) reacting a compound of formula III with two or more coupling agents to produce an activated compound; and
(ii) reacting the activated compound with an amine having the formula $(R^1_3C)_2NH$ to produce a compound of formula II.

The activated compound is the product of the reaction between the compound of formula III and the two or more coupling agents. Where the two or more coupling agents comprise carboxylic acid activating agents, the activated compound comprises an activated moiety, derived from the original carboxylic acid moiety of formula III, which is more likely to react with an amine than the original carboxylic acid moiety.

In some embodiments, the two or more coupling agents comprise a carboxylic acid activating agent. In some embodiments, the two or more coupling agents comprise an additive coupling agent. In some embodiments, the additive is capable of reacting with the product of the reaction of formula III and the coupling agent (the product being a compound comprising an activated moiety) to produce an activated compound comprising an even more activated moiety that is more likely to react with an amine than the original activated moiety.

Often, the two or more coupling agents comprise a carboxylic acid activating agent and an additive coupling agent.

In some embodiments, at least one of the two or more coupling agents is selected from the group consisting of carbodiimide coupling agents, phosphonium coupling agents and 3-(diethoxy-phosphoryloxy)-1,2,3-benzo[d]triazin-4(3H)-one (DEPBT), such as a carbodiimide coupling agent or a phosphonium coupling agent. In some embodiments, at least one of the two or more coupling agents is a carbodiimide coupling agent.

A carbodiimide coupling agent is a coupling agent which comprises a carbodiimide group R'—N=C=N—R", wherein R' and R" are hydrocarbyl groups optionally substituted with heteroatoms selected from nitrogen, sulfur and oxygen, typically nitrogen. Often, R' and R" are independently selected from $C_1$-$C_6$alkyl, $C_5$-$C_6$cycloalkyl, $C_1$-$C_6$alkylamino and morpholino$C_1$-$C_6$alkyl. Often, $C_1$-$C_6$alkyl is $C_3$alkyl, $C_5$-$C_6$cycloalkyl is cyclohexyl, $C_1$-$C_6$alkylamino is dimethylaminopropyl and/or morpholino$C_1$-$C_6$alkyl is morpholinoethyl.

In some embodiments, the carbodiimide coupling agent is any one selected from the group consisting of dicyclohexylcarbodiimide (DCC), diisopropylcarbodiimide (DIC), (N-(3-Dimethylaminopropyl)-N'-ethylcarbodiimide (EDC) and 1-cyclohexyl-(2- morpholinoethyl)carbodiimide metho-p-toluene sulfonate (CMCT). In some embodiments, the carbodiimide coupling agent is any one selected from the group consisting of dicyclohexylcarbodiimide (DCC), diisopropylcarbodiimide (DIC) and (N-(3-Dimethylaminopropyl)-N'-ethylcarbodiimide (EDC). Often, the carbodiimide coupling agent is N-(3-Dimethylaminopropyl)-N'-ethylcarbodiimide (EDC), typically as a hydrochloride salt (EDC.HCl). EDC or EDC.HCl are particularly preferred as they are non-toxic and are highly water soluble, facilitating their virtually complete removal in workup and wash steps of stage 1.

A phosphonium coupling agent comprises a phosphonium cation and a counterion, typically a hexafluorophosphate anion. In some embodiments, the phosphonium cation is of formula $[PR^a_3R^b]^+$ wherein Ra is di($C_1$-$C_6$)alkylamino or pyrrolidinyl and $R^b$ is halo or a hydrocarbyl group optionally substituted with nitrogen and/or oxygen atoms. Often, $R^b$ is bromo, benzotriazol-1-yloxy or 7-aza-benzotriazol-1-yloxy.

In some embodiments, the phosphonium coupling agent is any one selected from the group consisting of benzotriazol-1-yloxy-tris(dimethylamino)-phosphonium hexafluorophosphate (BOP), bromo-tripyrrolidino-phosphonium hexafluorophosphate (PyBrOP), benzotriazol-1-yloxy-tripyrrolidino-phosphonium hexafluorophosphate (PyBOP), 7-azabenzotriazol-1-yloxy-tripyrrolidinophosphonium hexafluorophosphate (PyAOP) and ethyl cyano(hydroxyimino)acetato-$O_2$) tri-(1-pyrrolidinyl)-phosphonium hexafluorophosphate (PyOxim).

In some embodiments, at least one of the two or more coupling agents is an additive coupling agent selected from the group consisting of 1-hydroxybenzotriazole (HOBt), hydroxy-3,4-dihydro-4-oxo-1,2,3-benzotriazine (HOOBt), Nhydroxysuccinimide (HOSu), 1-hydroxy-7-azabenzotriazole (HOAt), ethyl 2-cyano (hydroximino)acetate (Oxyma Pure), 4-(N,N-Dimethylamino)pyridine (DMAP), N-hydroxy-5-norbornene-2,3-dicarboximide (HONB), 6-chloro-1-hydroxybenzotriazole (6- Cl-HOBt), 3-hydroxy-4-oxo-3,4-dihydro-1,2,3-benzotriazine (HODhbt), 3-hydroxy-4-oxo3,4-dihydro-5-azabenzo-1,2,3-triazene (HODhat) and 3-hydroxyl-4-oxo-3,4-dihydro-5- azepine benzo-1,3-diazines (HODhad).

In some embodiments, at least one of the two or more coupling agents is an additive coupling agent selected from the group consisting of 1-hydroxybenzotriazole (HOBt), hydroxy-3,4-dihydro-4-oxo-1,2,3-benzotriazine (HOOBt), Nhydroxysuccinimide (HOSu), 1-hydroxy-7-azabenzotriazole (HOAt), ethyl 2-cyano-2-(hydroximino)acetate (Oxyma Pure) and 4-(N,N-Dimethylamino)pyridine (DMAP).

In some embodiments, at least one of the two or more coupling agents is an additive coupling agent which is 1-hydroxybenzotriazole.

In some embodiments, the two or more coupling agents consist of a coupling agent and an additive coupling agent wherein the coupling agent and additive coupling agent may be as described in the above embodiments.

A benefit of using both a coupling agent and an additive coupling agent is an increased rate of formation of compounds of formula II from compounds of formula III and an amine having the formula $(R^1_3C)_2NH$. In addition, when an additive coupling agent is used together with a carbodiimide coupling agent, the likelihood of unwanted side reactions may be reduced. For example, reaction of a compound of formula III with a carbodiimide coupling reagent is likely to form an O-acylisourea. This may undergo a rearrangement to form an N-acylurea, which is a stable compound unlikely to react with an amine. Additive coupling reagents may react with O-acylureas before rearrangement to N-acylureas, and produce compounds that go on to react with an amine, rather than inactive N-acylureas.

Therefore, in some embodiments, the two or more coupling agents consist of a carbodiimide coupling agent and an additive coupling agent.

In particular embodiments, the two or more coupling agents consist of N-(3- Dimethylaminopropyl)-N'-ethylcarbodiimide (EDC), typically as a hydrochloride salt (EDC.HCl), and 1-hydroxybenzotriazole (HOBt).

Often, an excess of coupling agent with respect to compound of formula III is used. In some embodiments, the ratio of coupling agent:compound of formula III is about 1:1 to about 3:1, typically about 1:1 to about 2:1 and most typically about 1:1 to about 1.5:1.

Often, an excess of additive coupling agent with respect to compound of formula III is used. In some embodiments, the ratio of additive coupling agent:compound of formula III is about 1:1 to about 3:1, typically about 1:1 to about 2:1 and most typically about 1:1 to about 1.5:1.

In some embodiments, where the two or more coupling agents comprise a coupling agent and an additive coupling agent, a ratio of coupling agent:compound of formula III and additive coupling agent:compound of formula III of about 1:1 to about 1.5:1 is used.

As described above, stage 1 comprises reacting the activated compound (the product of reacting a compound of formula III with two or more coupling agents) with an amine having the formula $(R^1_3C)_2NH$ to produce a compound of formula II. Each $R^1$ is independently selected from protium and deuterium. In some embodiments, each $R^1$ is protium, i.e. the amine is dimethylamine. In some embodiments, each $R^1$ is deuterium, i.e. the amine is dimethyl-$d_6$-amine.

The ratio of amine:compound of formula III employed in the method is often about 1:1. In some embodiments, the ratio of amine:compound of formula III is about 1:1 to about 3:1, typically about 1:1 to about 2:1.

In some embodiments, stage 1 further comprises isolating the compound of formula II. The skilled person is aware of techniques in the art suitable for isolation of a compound of formula II. For example, a compound of formula II may be extracted into an organic solvent such as dichloromethane or ethyl acetate, washed with an aqueous solution such as an aqueous basic solution, and concentrated. To increase purity, the isolated compound of formula II may be recrystallized. The skilled person is aware of techniques that are suitable for recrystallisation of compound of formula II. For example, the compound of formula II may be dissolved in the minimum amount of solvent at a particular temperature (e.g. at ambient temperature (e.g. about 15 to about 25° C.) or at elevated temperatures where heat is applied to the solution) and the resultant solution cooled to encourage precipitation. Alternatively, or in addition, the volume of the solution may be reduced to encourage precipitation, e.g. by simple evaporation at ambient temperature and pressure. Alternatively, or in addition, an anti-solvent may be used (in which the compound of formula II is less soluble than the solvent already present).

Isolated compounds of formula II are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer.

Typically, steps (i) and (ii) of stage 1 are carried out in a suitable solvent. The skilled person is able to assess which solvents are suitable for these steps. Examples of suitable solvents include dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). In some embodiments, steps (i) and (ii) of stage 1 are carried out in dichloromethane.

Steps (i) and (ii) of stage 1 are carried out at a suitable temperature and the skilled person is able to assess which temperatures are suitable for these steps. Often, steps (i) and (ii) of stage 1 are carried out at temperatures of about 10° C. to about 30° C. In some embodiments, steps (i) and (ii) of stage 1 are carried out at room temperature (about 20° C.).

In specific embodiments, stage 1 of the method of the invention comprises the steps of:
 i. contacting a compound of formula III and between about 1 and about 1.5 equivalents of an additive coupling agent, and between about 1 and about 1.5 equivalents of a carbodiimide coupling agent to produce a first composition; and
 ii. contacting the first composition with between about 1 and about 2 equivalents of an amine having the formula $(R^1_3C)_2NH$ to produce a second composition.

In some embodiments, about 1 g or more, such as about 1 g to about 100 kg or about 1 g to about 1 kg of a compound of formula III is employed in the method of the invention.

In some embodiments, the contacting of steps i. and ii. is carried out in the presence of a first solvent, such as between about 5 and about 20 volumes of a first solvent. The first solvent may be selected from any one of dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). Typically, the first solvent is DCM.

In some embodiments, step i. further comprises stirring or agitating the first composition. The first composition may be stirred or agitated for at least about 30 minutes, such as about 30 minutes to about 3 hours or about 30 minutes to about 2 hours, preferably at least about 1 hour, for example about 1 to about 3 hours or about 1 to about 2 hours. The first composition may be maintained at a temperature of between about 10° C. and about 30° C.

In some embodiments, the amine of step ii. is dissolved in a solvent, such as tetrahydrofuran (THF) or ether, prior to contacting. The amine may be present in the solvent at a concentration of about 2 M. Typically, the amine of step ii. is dissolved in THF.

In some embodiments, step ii. further comprises stirring or agitating the second composition. The second composition may be stirred or agitated for at least about 30 minutes, such about 30 minutes to about 3 hours or about 30 minutes to about 2 hours, preferably at least about 1 hour, for example about 1 to about 3 hours or about 1 to about 2 hours. The second composition may be maintained at a temperature of between about 10° C. and about 30° C.

In some embodiments, step ii. further comprises contacting the second composition with an aqueous basic solution to produce a third composition, for example contacting the second composition with between about 2 and about 10 volumes of an aqueous basic solution such as an aqueous solution comprising potassium carbonate.

In some embodiments, step ii. further comprises stirring or agitating the third composition. The third composition may be stirred or agitated for at least about 1 minute, such as about 1 to about 15 minutes or about 1 to about 10 minutes, preferably at least about 5 minutes, for example about 5 to about 15 minutes or about 5 to about 10 minutes. The third composition may be maintained at a temperature of between about 10° C. and about 30° C.

In some embodiments, where the third composition comprises an organic and an aqueous component, step ii. further comprises separating the organic component from the aqueous component. In some embodiments, the organic component is separated from the aqueous component within about 8 hours of the contacting of step i.

In even more specific embodiments, stage 1 of the method of the invention comprises the steps of:
 i. adding to a first vessel about 1 g or more of a compound of formula III and between about 1 and about 1.5 equivalents of an additive coupling agent,
 ii. adding to the first vessel between 5 and 20 volumes of a first solvent selected from DCM, acetone, IPA, iPrOAc, TBME, 2-MeTHF and EtOAc,
 iii. adding to the first vessel between about 1 and about 1.5 equivalents of a carbodiimide coupling agent,
 iv. stirring the contents of the first vessel for at least about 30 minutes, preferably at least about 1 hour (such as about 1 to about 2 hours), at between about 10° C. and about 30° C.,
 v. adding to the first vessel between about 1 and about 2 equivalents of an amine having the formula $(R^1_3C)_2NH$, wherein the amine is preferably dissolved in an ether solvent,
 vi. further stirring the contents of the first vessel for at least about 30 minutes, preferably at least about 1 hour (such as about 1 to about 2 hours), at between about 10° C. and about 30° C.,
 vii. adding to the first vessel between about 2 and about 10 volumes of an aqueous basic solution,
 viii. further stirring the contents of the first vessel for at least about 1 minute, preferably at least about 5 minutes (such as about 5 to about 10 minutes), at between about 10° C. and about 30° C.,
 ix. allowing an immiscible organic fraction to separate from an aqueous fraction, wherein the organic fraction comprises the compound of formula II, and
 x. removing the organic fraction comprising the compound of formula II,
wherein steps i. to x. are carried out within a single 8 hour period.

In some embodiments, the first solvent is DCM.

In some embodiments, the amine is dimethylamine. In some embodiments, the amine is dimethyl-$d_6$-amine. In some embodiments, the amine is dissolved in THF, for example at a concentration of about 2 M. In some embodiments, the amine is provided in the form of a salt, for example a hydrochloride salt, e.g. dimethylamine hydrochloride or dimethyl-$d_6$-amine hydrochloride.

In some embodiments, the aqueous basic solution comprises potassium carbonate.

In even more specific embodiments, stage 1 of the method of the invention further comprises the steps of:
xi. drying the organic fraction with a drying agent, for example a drying agent selected from calcium chloride, magnesium sulphate, and sodium sulphate,
xii. filtering the organic fraction,
xiii. concentrating the organic fraction, for example under vacuum such as under a pressure of less than about 1 atmosphere,
xiv. adding the concentrated organic fraction to a second vessel,
xv. adding between about 2 and about 10 volumes of a second solvent to the second vessel, wherein the second solvent is selected from IPA, EtOAc, IPrOAc, acetonitrile (MeCN), TBME, THF, 2-MeTHF and toluene,
xvi. stirring the contents of the second vessel for at least about 1 hour, preferably at least about 2 hours (such as about 2 to about 3 hours), at temperatures of between about 45° C. and about 55° C.,
xvii. cooling the contents of the second vessel to temperatures of between about 15° C. and about 25° C.,
xviii. filtering contents of the second vessel to obtain a filtrate, wherein the filtrate comprises the compound of formula II, and
xix. drying the filtrate.

In some embodiments, the drying agent of step xi. Is magnesium sulphate. In some embodiments, the solvent of step xv. Is selected from TBME and IPA.

Stage 2 comprises reacting the compound of formula II with $LiAlH_4$ and/or $LiAlD_4$ to produce a compound of formula I. As described above, $LiAlH_4$, $LiAlD_4$ or mixtures of the two may be reacted with the compound of formula II. In some embodiments, stage 2 comprises reacting the compound of formula II with $LiAlH_4$. In some embodiments, stage 2 comprises reacting the compound of formula II with $LiAlD_4$. In some embodiments, stage 2 comprises reacting the compound of formula II with a mixture of $LiAlH_4$ and $LiAlD_4$, for example a 50:50 mixture of $LiAlH_4$ and $LiAlD_4$.

Such mixtures may comprise $LiAlD_4$ and comprise between about 0.1 and about 99.9% hydride. Mixtures of between about 2% and about 98% lithium aluminium hydride or between about 2% and about 98% lithium aluminium deuteride may be employed. Sometimes, mixtures of $LiAlH_4$ and $LiAlD_4$ consist essentially of 98% $LiAlD_4$/ 2% $LiAlH_4$. Sometimes, such mixtures consist essentially of 95% $LiAlD_4$/5% $LiAlH_4$, 90% $LiAlD_4$/10% $LiAlH_4$, 85% $LiAlD_4$/15% $LiAlH_4$, 80% $LiAlD_4$/20% $LiAlH_4$, 75% $LiAlD_4$/25% $LiAlH_4$, 70% $LiAlD_4$/30% $LiAlH_4$, 65% $LiAlD_4$/35% $LiAlH_4$, 60% $LiAlD_4$/40% $LiAlH_4$, 55% $LiAlD_4$/45% $LiAlH_4$, 50% $LiAlD_4$/50% $LiAlH_4$, 45% $LiAlD_4$/55% $LiAlH_4$, 40% $LiAlD_4$/60% $LiAlH_4$, 35% $LiAlD_4$/65% $LiAlH_4$, 30% $LiAlD_4$/70% $LiAlH_4$, 25% $LiAlD_4$/75% $LiAlH_4$, 20% $LiAlD_4$/80% $LiAlH_4$, 15% $LiAlD_4$/85% $LiAlH_4$, 10% $LiAlD_4$/90% $LiAlH_4$, 5% $LiAlD_4$/95% $LiAlH_4$, or 2% $LiAlD_4$/98% $LiAlH_4$.

By the mixtures of $LiAlH_4$ and $LiAlD_4$ consisting essentially of specified percentages of $LiAlH_4$ and $LiAlD_4$ is meant that the mixture may comprise additional components (other than $LiAlH_4$ and $LiAlD_4$) but that the presence of these additional components will not materially affect the essential characteristics of the mixture. In particular, mixtures consisting essentially of $LiAlH_4$ and $LiAlD_4$ will not comprise material amounts of agents that are detrimental to the reduction of compounds of formula II to produce compounds of formula I (e.g. material amounts of agents that react with $LiAlH_4$ and $LiAlD_4$, compounds of formula II and/or compounds of formula I in a way that inhibits the reduction of compounds of formula II to produce compounds of formula I).

The amount of $LiAlH_4$ or $LiAlD_4$ comprised in mixtures of the two depends on the degree of deuteration sought in the compound of formula I. For example, where compounds of formula I are sought in which one $R^2$ is protium and the other is deuterium, a mixture of 50% $LiAlH_4$ and 50% $LiAlD_4$ may be preferred. Alternatively, where a mixture of compounds of formula I are sought, in which approximately half of the compounds comprise two deuterium atoms at the α-position (i.e. both $R^2$ are deuterium) and approximately half of the compounds comprise one deuterium atom and one protium atom at the α-position (i.e. one $R^2$ is deuterium and the other is protium), a mixture of 25% $LiAlH_4$ and 75% $LiAlD_4$ may be preferred.

The amount of $LiAlH_4$ and/or $LiAlD_4$ employed relative to compound of formula II is often 1:1. For the avoidance of doubt, the ratios of $LiAlH_4$ and/or $LiAlD_4$ relative to compound of formula II refer to the total amount of $LiAlH_4$ and/or $LiAlD_4$ used with respect to the amount of compound II. In some embodiments, the ratio of $LiAlH_4$ and/or $LiAlD_4$: compound of formula II is 0.5:1 to 1:1, such as 0.8:1 to 1:1. In some embodiments, the ratio of $LiAlH_4$ and/or $LiAlD_4$: compound of formula II is 0.9:1.

Typically, stage 2 is carried out in a suitable solvent. The skilled person is able to assess which solvents are suitable for stage 2. Examples of suitable solvents include ethers such as THF and diethyl ether. In some embodiments, stage 2 is carried out in THF. In some embodiments, the $LiAlH_4$ and/or $LiAlD_4$ is provided as a solution or suspension of $LiAlH_4$ and/or $LiAlD_4$ in a suitable solvent such as an ether, for example THF or diethyl ether, typically THF.

Stage 2 is carried out at a suitable temperature and the skilled person is able to assess which temperatures are suitable for these steps. Often, stage 2 is carried out at temperatures of about −5° C. to about 65° C.

In some embodiments, stage 2 further comprises isolating the compound of formula I. The skilled person is aware of techniques in the art suitable for isolation of a compound of formula I. For example, on quenching the reaction (e.g. with an aqueous solution of a tartrate salt such as Rochelle's salts), a compound of formula I may be extracted into an organic solvent such as an ether, e.g. THF or diethyl ether, washed with an aqueous solution such as an aqueous basic solution, and concentrated. The isolated compound of formula I may be recrystallized. The skilled person is aware of techniques that are suitable for recrystallisation of a compound of formula I. The examples of recrystallisation techniques described with respect to recrystallisation of a compound of formula II apply mutatis mutandis to recrystallisation of a compound of formula I.

In some embodiments, about 1 g or more, such as about 1 g to about 100 kg or about 1 g to about 1 kg of a compound of formula II is employed in stage 2.

In specific embodiments, stage 2 of the method of the invention comprises contacting a compound of formula II and between about 0.8 and about 1 equivalents, such as about 0.9 equivalents of $LiAlH_4$ and/or $LiAlD_4$ to produce a first composition. In some embodiments, the contacting is carried out in the presence of a solvent such as an ether, e.g. THF or diethyl ether, typically THF.

In some embodiments, the contacting comprises dropwise addition of $LiAlH_4$ and/or $LiAlD_4$ to a compound of formula II, wherein $LiAlH_4$ and/or $LiAlD_4$ is provided as a solution or suspension of $LiAlH_4$ and/or $LiAlD_4$ in a suitable solvent, such as an ether, e.g. THF or diethyl ether. In some embodiments, LiAlH$_4$ and/or LiAlD$_4$ is provided as a 2.4 M or 2 M solution or suspension of LiAlH$_4$ and/or LiAlD$_4$ in THF. In some embodiments, the LiAlH$_4$ and/or LiAlD$_4$ is provided as a 2 M solution or suspension of LiAlH$_4$ and/or LiAlD$_4$ in THF.

In some embodiments, the contacting is carried out at temperatures of about −5° C. to about 65° C.

In some embodiments, stage 2 further comprises stirring or agitating the first composition. The first composition may be stirred or agitated for about 1 hour to about 6 hours, typically for about 2 hours. The first composition may be stirred or agitated at a temperature of about 55° C. to about 65° C. In some embodiments, the first composition is stirred or agitated at a temperature of about 55° C. to about 65° C. and then cooled to temperatures of about 10° C. to about 30° C.

In some embodiments, the compound of formula II is contacted with about 0.9 equivalents of LiAlH$_4$ and/or LiAlD$_4$.

In specific embodiments, stage 2 comprises the steps of:
i. adding to a third vessel about 1 g or more (such as about 1 g to about 1 kg) of a compound of formula II,
ii. adding to the third vessel between about 5 and about 20 volumes of an ether solvent,
iii. adding to the third vessel, dropwise over at least about 15 minutes (e.g. about 15 to about 30 minutes), a solution of between about 0.8 and about 1 equivalents of LiAlH$_4$ and/or LiAlD$_4$ in the ether solvent at a temperature of between about −5° C. and about 65° C.,
iv. stirring the contents of the third vessel at between about 55° C. and about 65° C. for between about 1 hour and about 6 hours, preferably about 2 hours, and
v. cooling the contents of the third vessel to between 10° C. and 30° C., wherein the contents of the third vessel comprise a compound of formula I.

In some embodiments, the ether solvent is THF. In some embodiments, about 0.9 equivalents of LiAlH$_4$ and/or LiAlD$_4$ are added to the third vessel in step iii. The LiAlH$_4$ and/or LiAlD$_4$ is typically added to the third vessel as a 2.4 M or 2 M solution in THF. In some embodiments, the LiAlH$_4$ and/or LiAlD$_4$ is added to the third vessel as a 2 M solution in THF.

In even more specific embodiments, stage 2 comprises a workup comprising the steps of:
vi. adding between about 5 and about 20 volumes of an aqueous solution of a tartrate salt (such as Rochelle's salts) to a fourth vessel,
vii. adding a composition comprising crude compound of formula I, over at least about 15 minutes (such as about 15 minutes to about 1 hour), preferably at least about 30 minutes (such as about 30 minutes to about 1 hour), to the fourth vessel at between about 15° C. and about 25° C., and
viii. stirring the contents of the fourth vessel at between about 15° C. and about 25° C. for at least about 30 minutes (such as about 30 minutes to about 1 hour).

For the avoidance of doubt, the composition comprising crude compound of formula I refers to the contents of the third vessel on completion of step v. of stage 2, described above.

In further specific embodiments, stage 2 further comprises the steps of:
ix. allowing an organic fraction to separate from an aqueous fraction, wherein the organic fraction comprises the compound of formula III,
x. removing the aqueous fraction from the fourth vessel,
xi. adding between about 5 and about 20 volumes of a brine solution to the fourth vessel,
xii. stirring the contents of the fourth vessel at a temperature between about 15° C. and about 25° C. for at least about 5 minutes (such as about 5 to about 15 minutes),
xiii. removing the organic fraction comprising the compound of formula I as a freebase,
xiv. drying the organic fraction using a drying agent, such as a drying agent selected from calcium chloride, magnesium sulphate, and sodium sulphate,
xv. filtering the organic fraction, and
xvi. concentrating the organic fraction, for example under vacuum such as under a pressure of less than about 1 atmosphere.

Isolated compounds of formula I (produced via stage 2) are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer. In some embodiments, the compound of formula I is stored in a solvent, for example dissolved in ethanol. In some embodiments, the compound of formula I is stored in a solvent for more than about 8 hours, typically more than about 12 hours.

Compounds of formula I may alternatively be synthesised via a Fischer indole synthesis by reacting a compound of formula IV

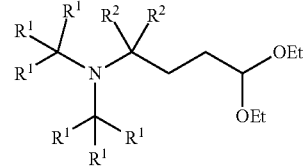

IV with a compound of formula V in the presence of an acid:

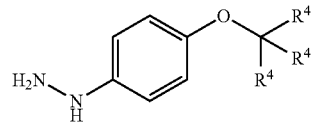

V wherein each $R^1$ is independently selected from protium and deuterium, each $R^2$ is independently selected from protium and deuterium, each $R^3$ is independently selected from protium and deuterium, and each $R^4$ is independently selected from protium and deuterium.

Preferably, the acid is sulfuric acid (H$_2$SO$_4$) or hydrochloric acid. Typically the acid is about 1% to about 10% H$_2$SO$_4$, about 4% H$_2$SO$_4$ is preferred.

Typically, synthesis of compounds of formula I from compounds of formula IV and V is carried out at a suitable temperature and the skilled person is able to assess which temperatures are suitable for this step. Preferably, this reaction is carried out at temperatures from about 20° C. to about 100° C., from about 30° C. to about 90° C., from about 40° C. to about 80° C., from about 50° C. to about 70° C., from about 60° C. to about 65° C. Typically the reaction is performed at reflux, i.e. about 100° C.

For the avoidance of doubt, embodiments related to the compound of formula I of the first, second and third aspects of the invention also apply mutatis mutandis to the compound of formula I (and thus compounds of formula IV and V) of this synthesis method.

Typically, synthesis of compounds of formula I from compounds of formula IV and V is carried out in a suitable solvent. The skilled person is able to assess which solvents are suitable for this step. Preferably, the solvent is water.

The reaction of compounds of formula IV with compounds of formula V may have a reaction time of from about 1 hour to about 48 hours. Preferably, the reaction time is from about 2 hours to about 40 hours, from 5 hours to about 30 hours, from about 10 hours to about 20 hours.

Synthesis of compounds of formula I may further comprise isolating the compound of formula I. The skilled person is aware of techniques in the art suitable for isolation of a compound of formula I. For example, a compound of formula I may be extracted into an organic solvent such as dichloromethane or ethyl acetate, washed with an aqueous solution such as an aqueous basic solution, and concentrated. The skilled person is aware of common laboratory techniques to increase the purity of compounds of formula I, for example, column chromatography or fractional distillation.

Typically, when both $R^2$ are protium or both $R^2$ are deuterium, compounds of formula IV may be synthesised via the Mannich reaction i.e. by contacting propargyl aldehyde diethyl acetal with $(R^1_3C)_2NH$ and formaldehyde $(H_2C=O)$ or deuterated formaldehyde $(D_2C=O)$ followed by catalytic hydrogenation. $(R^1_3C)_2NH$ may be dimethyl amine, dimethyl-$d_6$-amine, or $(D_3C)_2ND$. Catalytic hydrogenation may be carried out under an atmosphere of hydrogen using a hydrogenation catalyst. The hydrogenation catalyst may be, for example, palladium on barium sulfate, palladium on carbon or Raney-Nickel.

Typically, the synthesis of compounds of formula IV comprises the steps of:
a. Reacting propargyl aldehyde ethyl acetal with $(R^1_3C)_2NH$ and formaldehyde $(H_2C=O)$ or deuterated formaldehyde $(D_2C=O)$ to form a propargylic amine of formula VI.

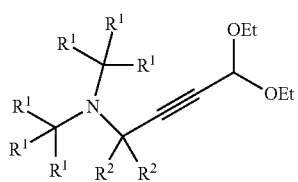

VI b. Reducing the compound of formula VI to form an compound of formula IV.

For the avoidance of doubt, embodiments related to the compound of formula I of the first, second and third aspects of the invention also apply mutatis mutandis to the compound of formula VI of this synthesis method.

Often, step i. is carried out under acidic conditions. The skilled person is aware of suitable acid catalysts for use in performing the reaction of step i. For example, the acid catalyst may be hydrochloric acid, hydrobromic acid, sulfuric acid. Alternatively, step i. may be catalysed by copper (II) acetate.

Typically, step i. is carried out at a suitable temperature and the skilled person is able to assess which temperatures are suitable for these steps. Suitable temperatures may be from about 0° C. to about 90° C. Preferably from about 5° C. to about 85° C., from about 10° C. to about 80° C., from about 20° C. to about 70° C., from about 30° C. to about 60° C., from about 40° C. to about 50° C.

Typically, step i. is carried out in a suitable solvent. The skilled person is able to assess which solvents are suitable for these steps. Suitable solvents include toluene, DCM, ethanol, DMSO, dioxane.

Step i. may further comprise isolating the compound of formula VI. The skilled person is aware of techniques in the art suitable for isolation of a compound of formula VI. For example, a compound of formula VI may be extracted into an organic solvent such as dichloromethane or ethyl acetate, washed with an aqueous solution such as an aqueous basic solution, and concentrated. The skilled person is aware of common laboratory techniques to increase the purity of compounds of formula VI, for example, column chromatography or fractional distillation.

Step ii. may be carried out under an atmosphere of hydrogen. The atmosphere of hydrogen may be at a pressure of from about 1 atm to about 4 atm, preferably at a pressure of about 1 atm.

Step ii. may be carried out in the presence of a hydrogenation catalyst. Suitable hydrogenation catalysts include palladium, platinum or nickel catalysts. Non-limiting examples include palladium on barium sulfate (Pd—$BaSO_4$), palladium on carbon (Pd—C), or Raney-Ni.

Typically, step ii. is carried out at a suitable temperature and the skilled person is able to assess which temperatures are suitable for this step. Preferably, step ii. is carried out at room temperature (about 20° C. to about 25° C.).

Typically, step ii. is carried out in a suitable solvent. The skilled person is able to assess which solvents are suitable for this step. Preferably, the solvent is ethanol.

Step ii. may further comprise isolating the compound of formula IV. The skilled person is aware of techniques in the art suitable for isolation of a compound of formula IV. For example, a compound of formula IV may be extracted into an organic solvent such as dichloromethane or ethyl acetate, washed with an aqueous solution such as an aqueous basic solution, and concentrated. The skilled person is aware of common laboratory techniques to increase the purity of compounds of formula IV, for example, column chromatography or fractional distillation.

Further alternatively, compounds of formula I may be synthesised by following the synthetic scheme provided in Scheme 1. For the avoidance of doubt, embodiments related to the compound of formula I of the first, second and third aspects of the invention also apply mutatis mutandis to the compound of formula I and starting materials/intermediates of this synthesis method.

Scheme 1

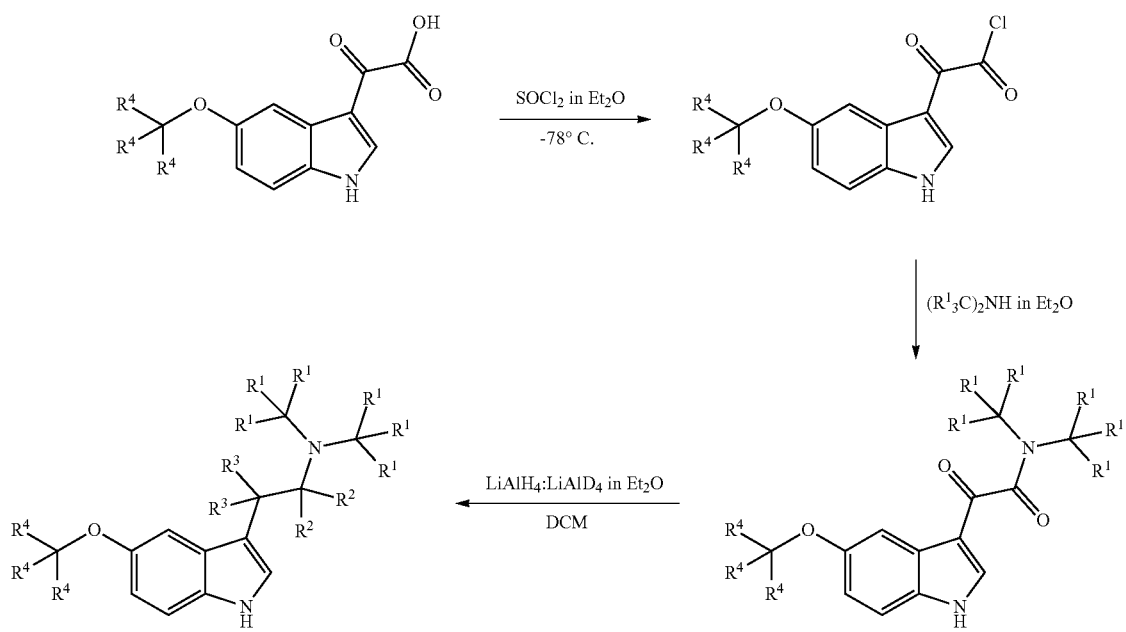

Each and every reference referred to herein is hereby incorporated by reference in its entirety, as if the entire content of each reference was set forth herein in its entirety.

EXAMPLES

The invention will now be demonstrated by reference to the following non-limiting examples.

Reagents were used as supplied unless otherwise stated.

Unless otherwise mentioned, room temperature and pressure are 20° C. (293.15 K, 68° F.) and 1 atm (14.696 psi, 101.325 kPa), respectively. For the purposes of the invention, measurements are made in these conditions unless otherwise mentioned.

High Performance Liquid Chromatography (HPLC) Parameters

System: Agilent 1100/1200 series liquid chromatograph or equivalent
Column: Triart Phenyl; 150×4.6 mm, 3.0 μm particle size (Ex: YMC, Part number: TPH12S03-1546PTH)
Mobile phase A: Water:Trifluoroacetic acid (100:0.05%)
Mobile phase B: Acetonitrile:Trifluoroacetic acid (100: 0.05%)

|  | Time | % A | % B |
|---|---|---|---|
| Gradient: | 0 | 95 | 5 |
|  | 13 | 62 | 38 |
|  | 26 | 5 | 95 |
|  | 30.5 | 5 | 95 |
|  | 31 | 95 | 5 |

| Flow rate: | 1.0 mL/min | Post runtime: | 4 minutes |
|---|---|---|---|
| Stop time: | 31 minutes | Wash vial: | N/A |
| Injection volume: | 5 μL | | |
| Column temperature: | 30° C. combined | | |
| Wavelength: | 200 nm, (4 nm) | Reference: | N/A |

Mass Spectrometry Parameters

Instrument: Agilent Technologies 6120 quadrupole LC/MS or equivalent
Column: Acquity BEH Phenyl; 30×4.6 mm, 1.7 μm particle size (Ex: Waters, Part number: 186004644)
Mobile phase A: Water:Trifluoroacetic acid (100:0.05%)
Mobile phase B: Acetonitrile:Trifluoroacetic acid (100: 0.05%)

|  | Time | % A | % B |
|---|---|---|---|
| Gradient: | 0 | 95 | 5 |
|  | 5.2 | 5 | 95 |
|  | 5.7 | 5 | 95 |
|  | 5.8 | 95 | 5 |
|  | 6.2 | 95 | 5 |

| Flow rate: | 1.0 mL/min | Post run time: | 2.3 minutes |
|---|---|---|---|
| Stop time: | 6.2 minutes | Wash vial: | N/A |
| Injection volume: | 5 μL | | |
| Column temperature: | 40° C. combined | | |
| MS parameters: | | | |
| Capillary Voltage: | 4000 V | | |
| Gas Temperature: | 350° C. | | |
| Nebuliser: | 35 psi | | |
| Gas Flow: | 12 L/min | | |

Scan collected between 218 and 232 m/z with the relevant chromatograms extracted from the data set.

Nuclear Magnetic Resonance (NMR)

$^1$H and $^{13}$C NMR spectra of the crystalline fumarate salt of a 5-methoxy-N,N-dimethyltryptamine compound were obtained using a Jeol ECX-400 spectrometer. The samples were dissolved in a suitable deuterated solvent for analysis. The data was acquired using Delta NMR Processing and Control Software version 4.3.

X-Ray Powder Diffraction (XRPD)

X-Ray Powder Diffraction patterns were collected on a PANalytical diffractometer using Cu Kα radiation (45 kV, Synthetic Methods
Stage 1 (D1 and D2 Route)

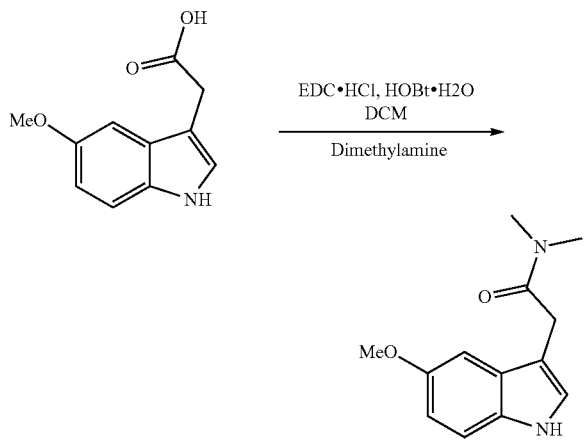

To a vessel under $N_2$ was charged 5-methoxyindole-3-acetic acid (1 equiv.), HOBt (~20% wet) (1.2 equiv.) and DCM (0.6 M) to give a milky white suspension. EDC.HCl (1.2 equiv.) was then charged portion-wise over 5 minutes at 16-22° C. The reaction mixture was stirred for 2 hours at ambient temperature before 2 M dimethylamine in THF (1.5 equiv.) was charged dropwise over 20 minutes at 20-30° C. The resultant solution was stirred at ambient temperature for 1 hour where HPLC indicated 0.22% 5-methoxyindole-3-acetic acid and 98.1% amide product stage 1. The reaction mixture was then charged with 10% $K_2CO_3$ and stirred for 5 minutes. The layers were separated, and the upper aqueous layer extracted twice with DCM. The organic extracts were combined and washed with saturated brine. The organic extracts were then dried over $MgSO_4$, filtered and concentrated in vacuo at 45° C. The crude material was then subjected to a slurry in TBME at 50° C. for 2 hours before being cooled to ambient temperature, filtered and washed with TBME. The filter-cake was then dried in vacuo at 50° C. to afford stage 1 19.9 g (yield=87%) as a light brown solid in a purity of 97.8% by HPLC and >95% by NMR.

Stage 2 (D1 MeO-DMT & D2 MeO-DMT)
D1 MeO-DMT

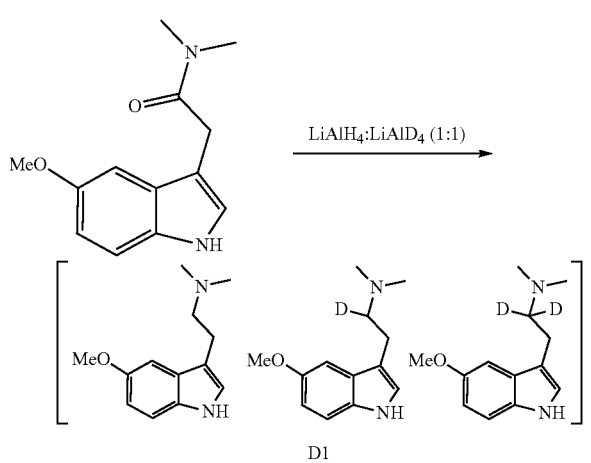

To a vessel under $N_2$ was charged stage 1 (1 equiv.) and THF (1 M) to give a pale yellow suspension. 2.4 M $LiAlH_4$ in THF and 2.4 M $LiAlD_4$ in THF (ratio of 1:1; 0.9 equiv. combined) was then charged dropwise over 35 minutes at 20-56° C. to give an amber solution. The solution was heated to 60° C. for 2 hours where HPLC indicated stage 1 not detectable (ND), stage 2 product 96.8%, impurity 2.1%. The complete reaction mixture was cooled to ambient temperature and then charged to a solution of 25% Rochelle's salts (aq.) dropwise over 30 minutes at 20-30° C. The resultant milky white suspension was allowed to stir at 20-25° C. for 1 hour after which the layers were separated and the upper organic layer washed with saturated brine solution. The organic layer was then dried over $MgSO_4$, filtered and concentrated in vacuo at 45° C. The resultant crude oil was subjected to an azeotrope from EtOH. This provided 8.8 g (7.5 g active; yield=87%) of stage 2 product as an amber oil in a purity of 94.4% by HPLC and >95% by NMR.

D2 MeO-DMT

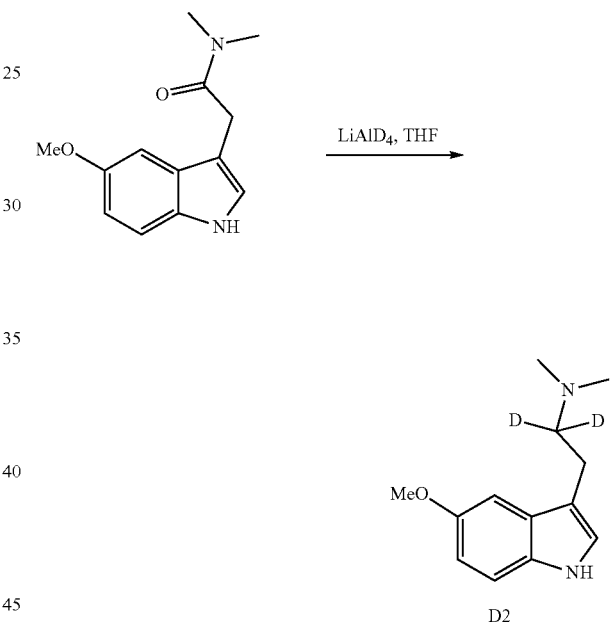

To a vessel under $N_2$ was charged stage 1 (1 equiv.) and THF (1 M) to give a pale yellow suspension. 2.4 M $LiAlD_4$ in THF (0.9 equiv.) was then charged dropwise over 35 minutes at 20-56° C. to give an amber solution. The solution was heated to 60° C. for 2 hours where HPLC indicated stage 1 not detectable (ND), stage 2 product 89.8%, impurity 5.6%. The reaction was heated for a further 1 hour, however there was no change in the completion profile. The complete reaction mixture was cooled to ambient temperature and then charged to a solution of 25% Rochelle's salts (aq.) dropwise over 30 minutes at 20-30° C. The resultant milky white suspension was allowed to stir at 20-25° C. for 1 hour after which the layers were separated and the upper organic layer washed with saturated brine solution. The organic layer was then dried over $MgSO_4$, filtered and concentrated in vacuo at 45° C. The resultant crude oil was subjected to an azeotrope from EtOH. This provided 8.25 g (6.7 g active; yield=78%) of stage 2 product as an amber oil in a purity of 89.4% by HPLC.

Stage 3 (D1 MeO-DMT Fumarate & D2 MeO-DMT Fumarate)
D1 MeO-DMT Fumarate (SPL029i)

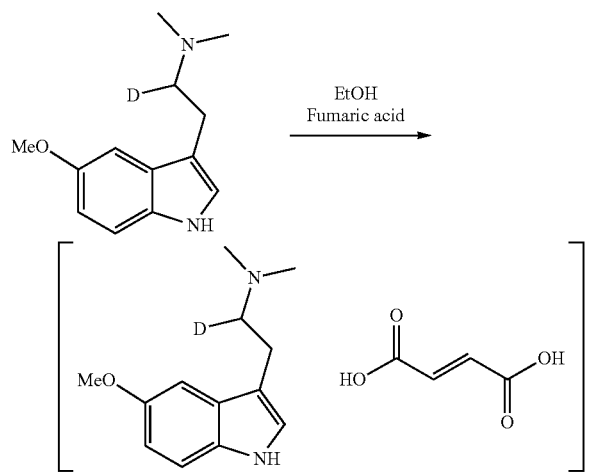

D₁ MeO-DMT Stage 2 (7.47 g, 34 mmol) and ethanol (74 ml) was charged to a flask under nitrogen and stirred to form a dark brown solution. Fumaric acid (4.6 g, 1.2 eq, 40 mmol) was charged and heated to 70° C. The reaction was stirred at 70° C. for 45 minutes. The reaction was cooled to room temperature over 1 hour, then cooled to 0-5° C. and stirred for a further 1 hour. The solids were filtered and washed with ethanol (40 ml) and dried in the oven at 50° C. over the weekend. 9.85 g (29 mmol; 86%) of an off-white solid was isolated as the mono-salt with 99.79% purity by HPLC. Deuteration levels are as follows:
D0—29.4%
D1—70.6%

D2 MeO-DMT Fumarate (SPL029h)

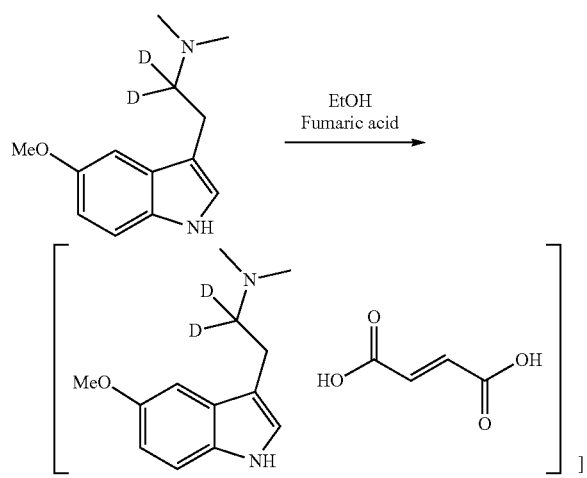

D2 MeO-DMT Stage 2 (6.8 g, 31 mmol) and ethanol (68 ml) was charged to a flask under nitrogen and stirred to form a dark brown solution. Fumaric acid (4.2 g, 1.2 eq, 36 mmol) was charged and heated to 70° C. The reaction was stirred at 70° C. for 45 minutes. The reaction was cooled to room temperature over 1 hour then cooled to 0-5° C. and stirred for a further 1 hour. The solids were filtered and washed with ethanol (40 ml) and dried in the oven at 50° C. over the weekend. Ethanol content by NMR was 0.89%, therefore the solids were returned to the oven for a further 3 days. 5.49 g (20 mmol; 64%) of a light brown solid was isolated as the hemi-salt with 99.11% purity by HPLC. Deuteration levels are as follows:
D0—0.1%
D1—3.2%
D2—96.7%

Stage 1 (D6 and D8 Route)

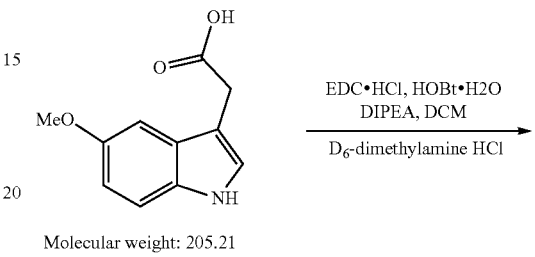

Molecular weight: 205.21

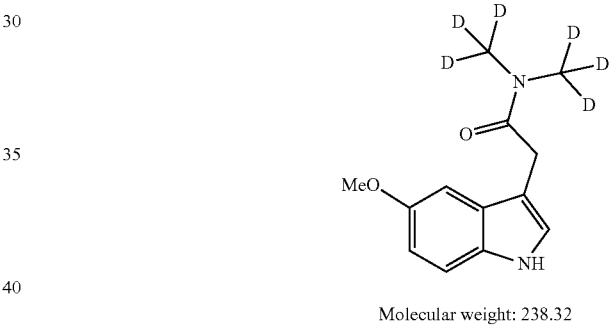

Molecular weight: 238.32

To a vessel under $N_2$ was charged 5-methoxyindole-3-acetic acid (1 equiv.), HOBt (~20% wet) (1.2 equiv.) and DCM (0.6 M) to give a milky white suspension. EDC.HCl (1.2 equiv.) was then charged portion-wise over 5 minutes at 16-22° C. The reaction mixture was stirred for 2 hours at ambient temperature before dimethyl-$d_6$-amine hydrochloride (1.5 equiv.) was charged dropwise over 20 minutes at 20-30° C. The resultant solution was stirred at ambient temperature for 1 hour where HPLC indicated 0.35% 5-methoxyindole-3-acetic acid and 97.2% amide product stage 1. The reaction mixture was then charged with 10% $K_2CO_3$ and stirred for 5 minutes. The layers were separated, and the upper aqueous layer extracted twice with DCM. The organic extracts were combined and washed with saturated brine. The organic extracts were then dried over $MgSO_4$, filtered and concentrated in vacuo at 45° C. The crude material was then subjected to a slurry in TBME at 50° C. for 2 hours before being cooled to ambient temperature, filtered and washed with TBME. The filter-cake was then dried in vacuo at 50° C. The amide product was then further purified by column chromatography to afford stage 1 product 21.62 g (yield=93%) as a yellow crystal in a purity of 98.4% by HPLC and >95% by NMR.

Stage 2 (D6 MeO-DMT & D8 MeO-DMT)
D6 MeO-DMT

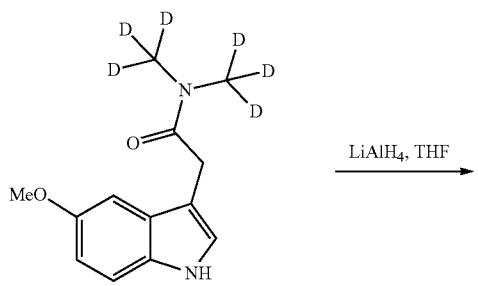

LiAlH₄, THF →

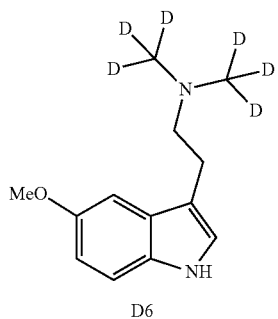

D6

To a vessel under N₂ was charged stage 1 (1 equiv.) and THF (1 M) to give a pale yellow suspension. 2.4 M LiAlH₄ in THF (0.9 equiv.) was then charged dropwise over 35 minutes at 20-56° C. to give an amber solution. The solution was heated to 60° C. for 2 hours where HPLC indicated stage 1 0.3%, stage 2 product 98.8%. The complete reaction mixture was cooled to ambient temperature and then charged to a solution of 25% Rochelle's salts (aq.) dropwise over 30 minutes at 20-30° C. The resultant milky white suspension was allowed to stir at 20-25° C. for 1 hour after which the layers were separated and the upper organic layer washed with saturated brine solution. The organic layer was then dried over MgSO₄, filtered and concentrated in vacuo at 45° C. The resultant crude oil was subjected to an azeotrope from EtOH. This provided 8.22 g (7.4 g active; yield=87.3%) of stage 2 product as an amber oil in a purity of 98.4% by HPLC.

D8 MeO-DMT

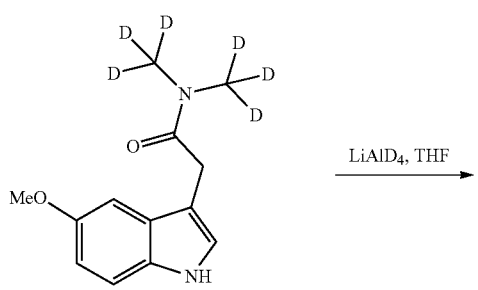

LiAlD₄, THF →

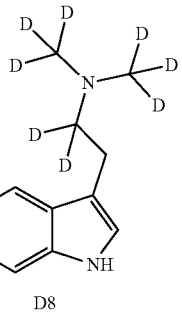

D8

To a vessel under N₂ was charged stage 1 (1 equiv.) and THF (1 M) to give a pale yellow suspension. 2.4 M LiAlD₄ in THF (0.9 equiv.) was then charged dropwise over 35 minutes at 20-56° C. to give an amber solution. The solution was heated to 60° C. for 2 hours where HPLC indicated stage 1 0.5%, stage 2 product 97.4%. The complete reaction mixture was cooled to ambient temperature and then charged to a solution of 25% Rochelle's salts (aq.) dropwise over 30 minutes at 20-30° C. The resultant milky white suspension was allowed to stir at 20-25° C. for 1 hour after which the layers were separated and the upper organic layer washed with saturated brine solution. The organic layer was then dried over MgSO₄, filtered and concentrated in vacuo at 45° C. The resultant crude oil was subjected to an azeotrope from EtOH. This provided 8.12 g (7.58 g active; yield=88.7%) of stage 2 product as an amber oil in a purity of 97.9% by HPLC.

[Stage 3 (D6 MeO-DMT Fumarate & D8 MeO-DMT Fumarate)
D6 MeO-DMT Fumarate (SPL029iii)

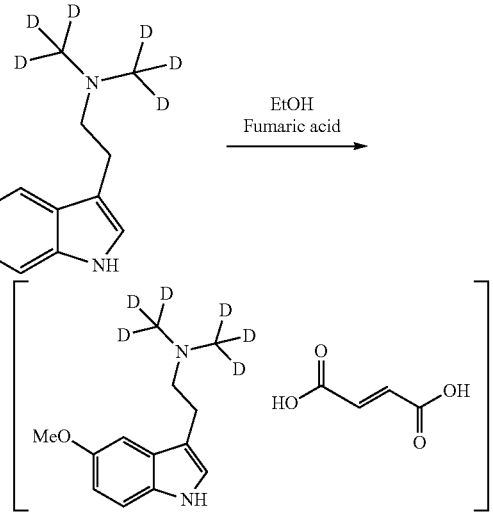

D6 MeO-DMT Stage 2 (7.40 g, 33 mmol) and ethanol (74 ml) was charged to a flask under nitrogen and stirred to form a dark brown solution. Fumaric acid (4.6 g, 1.2 eq, 39 mmol) was charged and heated to 70° C. The reaction was stirred at 70° C. for 30 minutes. The reaction was cooled to room temperature over 1 hour then cooled to 0-5° C. and stirred for a further 1 hour. The solids were filtered and washed with ethanol (40 ml) and dried in the oven at 50° C. overnight. 6.04 g (21 mmol; 65%) of an off-white solid was isolated as the hemi-salt with 99.61% purity by HPLC. Deuteration levels are as follows:

D0—not detectable
D5—0.4%
D6—99.6%
D8 MeO-DMT Fumarate (SPL029iv)

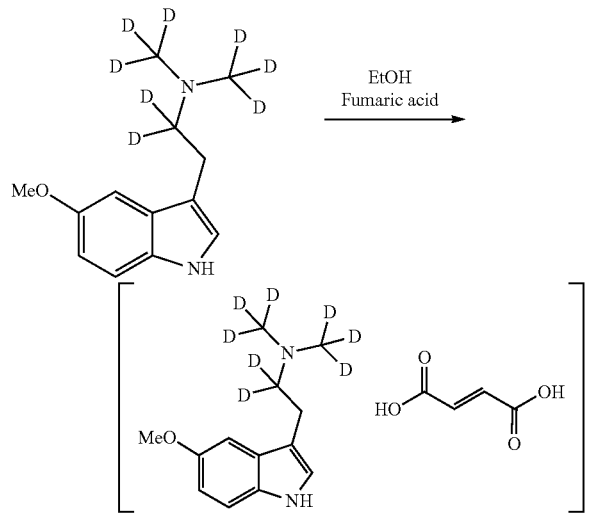

D8 MeO-DMT Stage 2 (7.58 g, 33 mmol) and ethanol (76 ml) was charged to a flask under nitrogen and stirred to form a dark brown solution. Fumaric acid (4.7 g, 1.2 eq, 40 mmol) was charged and heated to 70° C. The reaction was stirred at 70° C. for 30 minutes. The reaction was cooled to room temperature over 2 hour then cooled to 0-5° C. and stirred for a further 1 hour. The solids were filtered and washed with ethanol (40 ml) and dried in the oven at 50° C. overnight. 9.60 g (28 mmol; 84%) of an off-white solid was isolated as the mono-salt with 99.71% purity by HPLC. Deuteration levels are as follows:
D0—not detectable
D6—3.9%
D7—3.2%
D8—92.8%

The invention claimed is:

1. A crystalline fumarate salt of a compound having a Formula I:

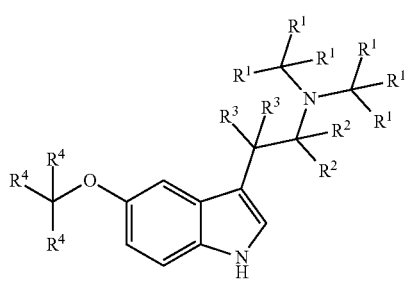

wherein:
each $R^1$ is independently selected from protium and deuterium;
each $R^2$ is independently selected from protium and deuterium;
each $R^3$ is independently selected from protium and deuterium; and
each $R^4$ is independently selected from protium and deuterium; and
wherein the crystalline fumarate salt has a PXRD pattern comprising characteristic peaks at 19.2±0.2 and 24.7±0.2 degrees 2-theta.

2. The crystalline fumarate salt of claim 1, wherein the compound has a PXRD pattern further comprising characteristic peaks at 18.2±0.2 degrees 2-theta.

3. The crystalline fumarate salt of claim 1, wherein one or more $R^1$ is deuterium.

4. The crystalline fumarate salt of claim 1, wherein each $R^1$ is deuterium.

5. The crystalline fumarate salt of claim 1, wherein one or more $R^2$ is deuterium.

6. The crystalline fumarate salt of claim 1, wherein each $R^2$ is deuterium.

7. The crystalline fumarate salt of claim 1, wherein one or more $R^3$ is protium.

8. The crystalline fumarate salt of claim 1, wherein each $R^3$ is protium.

9. The crystalline fumarate salt of claim 1, wherein one or more $R^4$ is protium.

10. The crystalline fumarate salt of claim 1, wherein each $R^4$ is protium.

11. The crystalline fumarate salt of claim 1, wherein each $R^1$ is protium, each $R^2$ is protium, each $R^3$ is protium, and each $R^4$ is protium.

12. The crystalline fumarate salt of claim 1, wherein each $R^1$ is protium, one $R^2$ is protium and one $R^2$ is deuterium, each $R^3$ is protium, and each $R^4$ is protium.

13. The crystalline fumarate salt of claim 1, wherein each $R^1$ is protium, each $R^2$ is deuterium, each $R^3$ is protium, and each $R^4$ is protium.

14. The crystalline fumarate salt of claim 1, wherein each $R^1$ is deuterium, each $R^2$ is protium, each $R^3$ is protium, and each $R^4$ is protium.

15. The crystalline fumarate salt of claim 1, wherein each $R^1$ is deuterium, each $R^2$ is deuterium, each $R^3$ is protium, and each $R^4$ is protium.

16. A method of producing the crystalline fumarate salt of claim 1, comprising:
forming an ethanolic solution of a compound having Formula I;
contacting the ethanolic solution with fumaric acid to form a mixture;
stirring the mixture for between about 15 and about 45 minutes; and
cooling the mixture to between about 5° C. and about 0° C.

17. The method of claim 16, further comprising adding seed crystals of the crystalline fumarate salt of claim 1.

18. A method of treating a psychiatric or neurological disorder which is major depressive disorder or treatment resistant depression comprising administering to a patient in need thereof a pharmaceutically acceptable formulation comprising the crystalline fumarate salt of claim 1.

19. The method of claim 18, wherein:
each $R^1$ is protium, each $R^2$ is protium, each $R^3$ is protium, and each $R^4$ is protium;
each $R^1$ is protium, one $R^2$ is protium and one $R^2$ is deuterium, each $R^3$ is protium, and each $R^4$ is protium;
each $R^1$ is protium, each $R^2$ is deuterium, each $R^3$ is protium, and each $R^4$ is protium;
each $R^1$ is deuterium, each $R^2$ is protium, each $R^3$ is protium, and each $R^4$ is protium; or
each $R^1$ is deuterium, each $R^2$ is deuterium, each $R^3$ is protium, and each $R^4$ is protium.

* * * * *